United States Patent
Zhu et al.

(10) Patent No.: US 7,801,598 B2
(45) Date of Patent: Sep. 21, 2010

(54) DEVICE AND METHOD FOR THE DETERMINATION OF DRY WEIGHT BY CONTINUOUS MEASUREMENT OF RESISTANCE AND CALCULATION OF CIRCUMFERENCE IN A BODY SEGMENT USING SEGMENTAL BIOIMPEDANCE ANALYSIS

(75) Inventors: Fansan Zhu, Flushing, NY (US); Nathan W. Levin, New York, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1384 days.

(21) Appl. No.: 11/246,635

(22) Filed: Oct. 7, 2005

(65) Prior Publication Data

US 2006/0122540 A1 Jun. 8, 2006

Related U.S. Application Data

(63) Continuation-in-part of application No. 10/305,513, filed on Nov. 27, 2002, now Pat. No. 7,228,170, which is a continuation-in-part of application No. 09/638,657, filed on Aug. 14, 2000, now Pat. No. 6,615,077.

(60) Provisional application No. 60/617,339, filed on Oct. 7, 2004.

(51) Int. Cl.
*A61B 5/05* (2006.01)
*A61B 5/103* (2006.01)
*A61B 5/117* (2006.01)

(52) U.S. Cl. ..................................... 600/547; 600/595
(58) Field of Classification Search ................. 600/547, 600/595

See application file for complete search history.

(56) References Cited

U.S. PATENT DOCUMENTS

| | | | | |
|---|---|---|---|---|
| 4,793,362 | A * | 12/1988 | Tedner | 600/547 |
| 5,720,296 | A * | 2/1998 | Cha | 600/554 |
| 6,125,297 | A * | 9/2000 | Siconolfi | 600/547 |
| 6,228,033 | B1 * | 5/2001 | Koobi et al. | 600/483 |
| 6,615,077 | B1 | 9/2003 | Zhu et al. | |
| 2002/0112898 | A1 * | 8/2002 | Honda et al. | 177/245 |
| 2003/0120170 | A1 | 6/2003 | Zhu et al. | |
| 2004/0064063 | A1 * | 4/2004 | Chamney | 600/547 |
| 2005/0039763 | A1 * | 2/2005 | Kraemer et al. | 128/920 |
| 2008/0086058 | A1 * | 4/2008 | Chamney et al. | 600/547 |

* cited by examiner

*Primary Examiner*—Max Hindenburg
*Assistant Examiner*—Adam J Eiseman
(74) *Attorney, Agent, or Firm*—Kenyon & Kenyon LLP

(57) ABSTRACT

A method and device for continuously calculating the circumference of a body segment is based on the continuous measurement of the extracellular resistance of the body segment. Also disclosed is a method and device for determining the dry weight of a dialysis patient wherein the time at which the dry weight of the patient has been achieved is identified as the time at which the patient's normalized resistivity as a function of time ($\rho_N(t)$) is greater than or equal to a minimum level of normalized resistivity in healthy subjects ($\rho_{N,H}$).

9 Claims, 11 Drawing Sheets

Correlation of circumference of calf post HD between measurement and calculation

DEVICE AND METHOD FOR THE DETERMINATION OF DRY WEIGHT BY CONTINUOUS MEASUREMENT OF RESISTANCE AND CALCULATION OF CIRCUMFERENCE IN A BODY SEGMENT USING SEGMENTAL BIOIMPEDANCE ANALYSIS

CROSS-REFERENCE TO RELATED APPLICATIONS

This application claims the benefit of U.S. Provisional Application No. 60/617,339 (filed Oct. 7, 2004), and this application is also a continuation-in-part of prior U.S. patent application Ser. No. 10/305,513 (filed Nov. 27, 2002), now U.S. Pat. No. 7,228,170, which is a continuation-in-part of prior U.S. patent application Ser. No. 09/638,657 (filed Aug. 14, 2000), now U.S. Pat. No. 6,615,077. Each of these aforementioned applications are incorporated herein by reference in their entireties.

FIELD OF THE INVENTION

The present invention relates to a device and method that utilize segmental bioimpedance for the determination of dry weight by the continuous measurement of resistance and calculation of circumference in a body segment.

BACKGROUND OF THE INVENTION

Accurate assessment of a dialysis patient's hydration status and prediction of dry body weight (DW or dry weight) is a major problem in the clinical management of the dialysis patient. In both hemodialysis and peritoneal dialysis patients, dry weight is the target weight at the end of dialysis treatment which best reflects removal of excess water from the body. In clinical practice, estimation of DW is an imprecise undertaking, and depends to a large extent on the treating physician's interpretation, based on his or her medical experience and familiarity with the particular patient's condition, of clinical symptoms and signs such as changes in the blood pressure, pulse, and weight of the patient. The correct interpretation of such signs and symptoms is complicated by the fact that the pre-treatment body weight varies for each treatment, the amount of excess fluid is not constant and the amount of fluid that can or should be removed from any particular patient during any particular dialysis treatment may be limited by an individual's cardiovascular tolerance, often manifested by clinical signs and symptoms, such as pretibial edema, dyspnea, cramps and/or a decline in blood pressure. Alternatively, an overestimation of the amount of fluid to be removed may result in potentially avoidable symptoms, unnecessarily lengthy dialysis treatments and often prolonged stays at the dialysis facility. Therefore, over- or underestimation of DW will significantly affect both the efficiency of dialysis treatment and patients' quality of life.

Bioelectrical impedance analysis (BIA) has been recognized as a noninvasive and simple technique to measure body hydration and hydration status (i.e. over-, under- or normal hydration) of subjects for more than twenty years. There is substantial literature on using BIA for the study of dry weight. Kouw et al proposed a method to measure changes in regional conductivity, and then to measure regional extracellular volume (ECV) and intracellular volume (ICV) by BIA. See, P. M. Kouw, et al., *Assessment of post-dialysis dry weight: an application of the conductivity measurement method*. Kidney Int. 41:440-444,1992. However, Kouw's method cannot be used to measure interstitial fluid alone as it does not distinguish between interstitial fluid and plasma, both of which make up the ECV compartment. Piccoli published a method of BIA vector analysis which uses the ratio of resistance to reactance to identify dry weight. While this technique could be used to compare the subjects' body hydration, it is unable to predict individual patient's dry weight because of the significant variation in measured values. See, Piccoli A: *Identification of operational clues to dry weight prescription in hemodialysis using bioimpedance vector analysis*. Kidney Int. 5 3:1036-1043,1998.

Recently, there have been increased numbers of dry weight studies using blood volume (BV) measurements. See, for example, J. P. de Vries et al, *Non-invasive monitoring of blood volume during hemodialysis: Its relation with post-dialytic dry weight*. Kidney Int 44:851-854,1993, and J. K. Leypold, et al, *Determination of circulating blood volume by continuously monitoring hematocrit during hemodialysis*. J. Am. Soc. Nephrol. 6:214-219,1995. Blood volume measurement is a noninvasive technique that can be used to indicate water concentration in blood, i.e. hematocrit, during hemodialysis, but it cannot be used to directly determine dry weight because changes in blood volume are mainly dependent on the rate of vascular refilling which, in part, is independent of body hydration. See, e.g., J. K. Leypoldt, et al, *Evaluating volume status in hemodialysis patients*. Adv. Ren. Replace. Ther. 5:64-74, 1998. On the other hand, since a change in the hematocrit level may alter conductivity in the blood during dialysis, it is difficult to obtain information about tissue hydration by either traditional bioelectrical impedance analysis or blood volume analysis. To date, a major problem has been how to measure resistivity of blood and tissue separately, in order to estimate the fluid volume in the intravascular compartment and the interstitial compartment, respectively.

Thus, there is a need for a precise, easily used and operator independent method for determining the hydration status of a dialysis patient, identifying or predicting the dry weight of such a patient and calculating the amount of fluid that should be removed during a dialysis session.

SUMMARY OF THE INVENTION

The present invention includes a device for continuously calculating the circumference of a body segment, the device comprising: a digital signal processor; an electrical output means being in electrical communication with the digital signal processor and being attachable to the body segment, the electrical output means being adapted to apply electrical current to the body segment; an electrical input means being in electrical communication with the digital signal processor and being attachable to the body segment, the electrical input means being adapted to receive the current transmitted through the body segment and transmit the same to the digital signal processor; and a microprocessor being in electrical communication with the digital signal processor; wherein the microprocessor is adapted to continuously calculate the circumference of the body segment based on the continuous measurement of the extracellular resistance of the body segment. In one embodiment of the device, the microprocessor continuously calculates the circumference of the body segment according to the following equation:

$$\chi_t = \sqrt{\chi_0^2 - \frac{4\pi\rho_0 L}{R_0}\left(1 - \frac{R_0}{R_t}\right)}$$

wherein $\chi_t$ is the circumference of the body segment as a function of time; $\chi_0$ is the initial circumference of the body segment; $\rho_0$ is a constant value of resistivity; L is the length of the body segment; $R_0$ is the initial extracellular resistance of the body segment; and $R_t$ is the extracellular resistance of the body segment as a function of time.

The present invention also includes a method of continuously calculating the circumference of a body segment, the method comprising: continuously measuring the extracellular resistance of the body segment; and continuously calculating the circumference of the body segment based on the continuous measurement of the extracellular resistance of the body segment. In one embodiment of the method, the circumference of the body segment is continuously calculated according to the following equation:

$$\chi_t = \sqrt{\chi_0^2 - \frac{4\pi\rho_0 L}{R_0}\left(1 - \frac{R_0}{R_t}\right)}$$

wherein $\chi_t$ is the circumference of the body segment as a function of time; $\chi_0$ is the initial circumference of the body segment; $\rho_0$ is a constant value of resistivity; L is the length of the body segment; $R_0$ is the initial extracellular resistance of the body segment; and $R_t$ is the extracellular resistance of the body segment as a function of time.

In accordance with the present invention, the method of continuously calculating the circumference of a body segment can be used in a wide variety of applications. For example, the body segment can be that of a dialysis patient, and a change in the circumference of the body segment can be due to a change in the fluid volume during a dialysis treatment. In addition, a change in the circumference of the body segment can be due to an internal bleeding of the body segment, and the change in circumference can be used to detect swelling of a body segment caused by bleeding inside the body. Furthermore, in addition to continuously calculating the circumference of a body segment of human beings, the method of the invention may also be used to continuously calculate the circumference of a body segment of an animal's body.

The present invention also provides a method for determining a dialysis patient's dry weight comprising the steps of: continuously measuring the extracellular resistance of a body segment during dialysis and graphing the ratio of $R_0/R_t$ as a function of time, wherein $R_0$ is the extracellular resistance at the start of dialysis and $R_t$ is the extracellular resistance as a function of time; flattening the graph of the ratio of $R_0/R_t$ as a function of time; comparing the patient's normalized resistivity as a function of time ($\rho_N(t)$) to a minimum level of normalized resistivity in healthy subjects ($\rho_{N,H}$); identifying the time at which the dry weight of the patient has been achieved when $\rho_N(t) \geqq \rho_{N,H}$; and calculating the patient's dry weight.

In one embodiment of the method, the patient's normalized resistivity as a function of time ($\rho_N(t)$) is calculated according to the following equation:

$$\rho_N(t) = \frac{\rho(t)}{BMI} \times 10^{-2} \Omega \cdot m^3/kg$$

wherein BMI is the patient's body mass index defined as body weight divided by body height squared; and $\rho(t)$ is the resistivity of the body segment as a function of time, calculated according to the following equation:

$$\rho(t) = \frac{\chi_t^2 \cdot R_t}{4\pi L} \Omega \cdot cm$$

wherein L is the length of the body segment; and $\chi_t$ is the circumference of the body segment as a function of time which is continuously calculated according to the following equation:

$$\chi_t = \sqrt{\chi_0^2 - \frac{4\pi\rho_0 L}{R_0}\left(1 - \frac{R_0}{R_t}\right)}$$

wherein $\chi_0$ is the initial circumference of the body segment; and $\rho_0$ is a constant value of resistivity.

One embodiment of the method includes the patient's dry weight (DW) being calculated according to the following equation:

$$DW = W_{pre} - \int_{t_0}^{t_{DW}} UFR(t) \cdot dt$$

where $W_{pre}$ is the patient's body weight prior to dialysis; UFR(t) is the ultrafiltration rate (UFR) as a function of time during dialysis, with $t_0$ to $t_{DW}$ being the time interval of a functioning UFR in which $t_0$ is the start time of dialysis and $t_{DW}$ is the time at which the dry weight of the patient is achieved.

According to an embodiment of the method, the flattening of the graph of the ratio of $R_0/R_t$ as a function of time is achieved during a time interval $\Delta t$ in accordance with at least one of the following equations:

$\delta(\Delta t) < C_1$;

and $k_s = \delta(\Delta t)/\Delta t < C_2$;

wherein $\lambda(t)$ $R_0/R_t$; $\delta(\Delta t) = \lambda(t) - \lambda(t + \Delta t)$; and $C_1$ and $C_2$ are constants; and wherein the flattening of the graph of the ratio of $R_0/R_t$ as a function of time is confirmed during the time interval $\Delta t$ by an algorithm of least squares.

In addition, the present invention includes a device for determining the dry weight of a dialysis patient comprising: a digital signal processor; an electrical output means being in electrical communication with the digital signal processor and being attachable to a body segment, the electrical output means being adapted to apply electrical current to the body segment; an electrical input means being in electrical communication with the digital signal processor and being attachable to a body segment, the electrical input means being adapted to receive the current transmitted through the body segment and transmit the same to the digital signal processor; and a microprocessor being in electrical communication with the digital signal processor. The microprocessor is adapted to: continuously measure an extracellular resistance of the body segment during dialysis and graph the ratio of $R_0/R_t$ as a function of time, wherein $R_0$ is the extracellular resistance at the start of dialysis and $R_t$ is the extracellular resistance as a function of time; flatten the graph of the ratio of $R_0/R_t$ as a function of time; compare the patient's normalized resistivity as a function of time ($\rho_N(t)$) to a minimum level of normalized resistivity in healthy subjects ($\rho_{N,H}$); identify the time at which the dry weight of the patient has been achieved when $\rho_N(t) \geq \rho_{N,H}$; and calculate the patient's dry weight.

In one embodiment of the device, the patient's normalized resistivity as a function of time ($\rho_N(t)$) is calculated according to the following equation:

$$\rho_N(t) = \frac{\rho(t)}{BMI} \times 10^{-2} \Omega \cdot m^3/kg$$

wherein BMI is the patient's body mass index defined as body weight divided by body height squared; and $\rho(t)$ is the resistivity of the body segment as a function of time, calculated according to the following equation:

$$\rho(t) = \frac{\chi_t^2 \cdot R_t}{4\pi L} \Omega \cdot cm$$

wherein L is the length of the body segment; and $\chi_t$ is the circumference of the body segment as a function of time which is continuously calculated according to the following equation:

$$\chi_t = \sqrt{\chi_0^2 - \frac{4\pi \rho_0 L}{R_0}\left(1 - \frac{R_0}{R_t}\right)}$$

wherein $\chi_0$ is the initial circumference of the body segment; and $\rho_0$ is a constant value of resistivity.

One embodiment of the device includes the patient's dry weight (DW) being calculated according to the following equation:

$$DW = W_{pre} - \int_{t_0}^{t_{DW}} UFR(t) \cdot dt$$

where $W_{pre}$ is the patient's body weight prior to dialysis; UFR(t) is the ultrafiltration rate (UFR) as a function of time during dialysis, with $t_0$ to $t_{DW}$ being the time interval of a functioning UFR in which $t_0$ is the start time of dialysis and $t_{DW}$ is the time at which the dry weight of the patient is achieved.

According to an embodiment of the device, the flattening of the graph of the ratio of $R_0/R_t$ as a function of time is achieved during a time interval $\Delta t$ in accordance with at least one of the following equations:

$\delta(\Delta t) \leq C_1$;

and $k_s = \delta(\Delta t)/\Delta t < C_2$;

wherein $\lambda(t) = R_0/R_t$; $\delta(\Delta t) = \lambda(t) - \lambda(t+\Delta t)$; and $C_1$ and $C_2$ are constants; and wherein the flattening of the graph of the ratio of $R_0/R_t$ as a function of time is confirmed during the time interval $\Delta t$ by an algorithm of least squares.

Other objects, features and advantages of the invention will be readily apparent from the following detailed description of a preferred embodiment thereof taken in conjunction with the drawings.

BRIEF DESCRIPTION OF THE FIGURES

FIG. 1A represents the situation in which no external pressure is applied to the segment and the blood vessels are uncompressed. FIG. 1B illustrates the situation in which external pressure is applied to the segment and the blood vessels are compressed.

DETAILED DESCRIPTION OF THE INVENTION

The present invention provides a method of determining hemodialysis and peritoneal dialysis patients' hydration status, or more specifically, dry weight, to facilitate the appropriate dialysis prescription. The invention comprises a means of determining and monitoring the resistivity and/or resistance of the patient's body or body segment, and hence the correct dry weight or desired hydration status of a patient undergoing dialysis. The invention further provides a method for determining and monitoring various physiologic parameters of the patient undergoing dialysis, including but not limited to the circumference of a body segment.

From a physiological point of view, in healthy people the amount of fluid in the interstitial compartment should be a relatively constant value within a small range. Thus, this value should be the criterion to indicate the degree of a patient's body hydration.

We have found that the refilling volume of a peripheral body segment, such as an arm (upper extremity) or leg (lower extremity), is an important indicator of a dialysis patient's hydration status or dry body weight. In one aspect, the present invention provides a means to separately measure, by segmental bioimpedance analysis (SBIA), the degree of regional body hydration, including fluid volume in the interstitial compartment and the intravascular compartment, in order to determine a patient's fluid status and dry body weight.

Figure 1B:
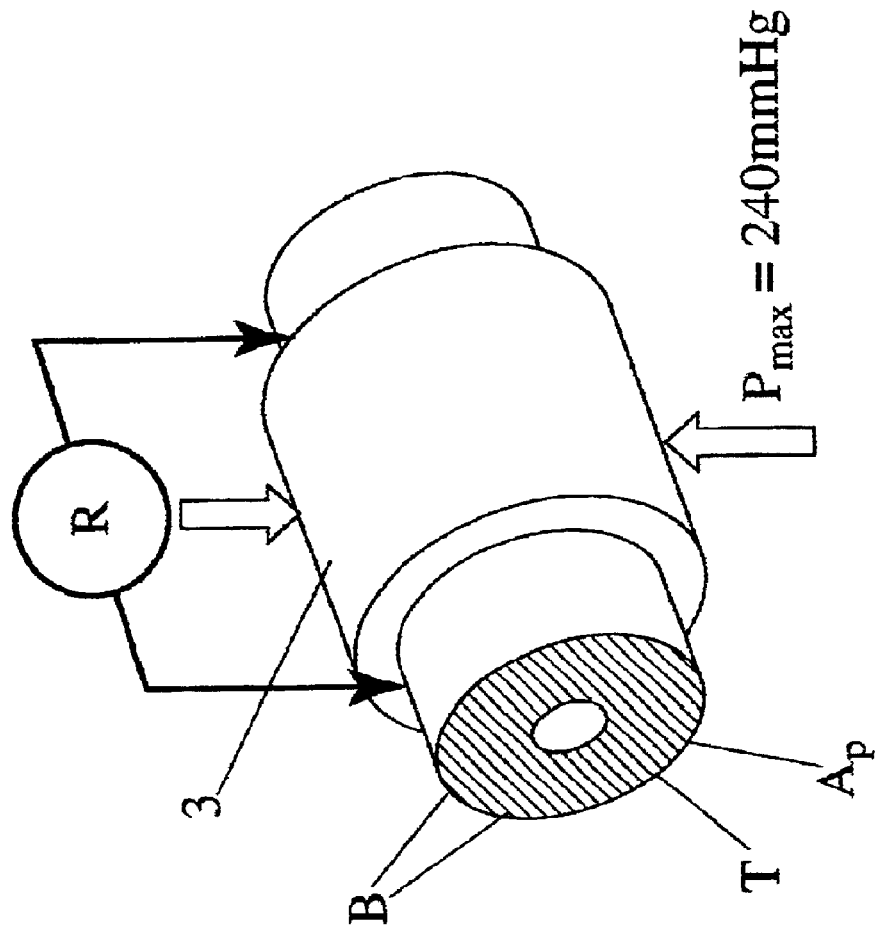
FIGS. 1A and 1B each represent a stylized 3-dimensional view of a body segment, that illustrates the principle of measuring resistivity according to one embodiment of the present invention.
Figure 1A:
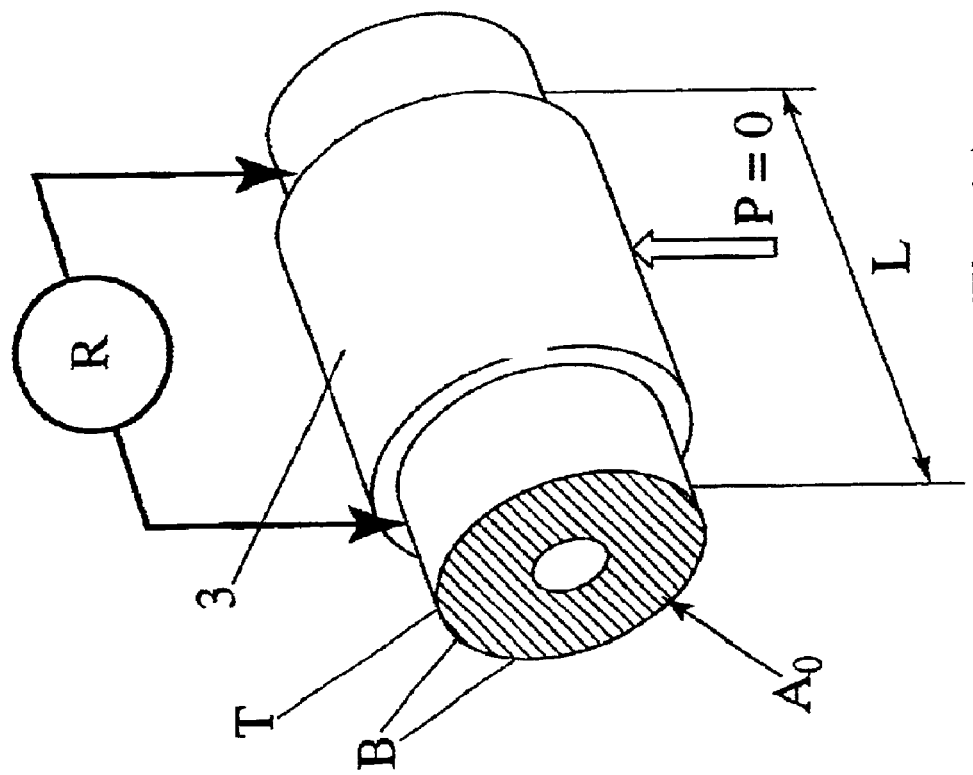

One preferred embodiment of the present invention comprises a means to continuously measure the resistivity and/or resistance of a body segment. The body segment may be the whole body, preferably a limb segment, more preferably a leg or arm segment, and most preferably a calf segment. As shown in FIG. 1A, the resistivity and/or resistance of a body segment is measured by the placement of measurement electrodes at points L1 and L2, separated by a distance L. One of skill in the art will appreciate that while distance L may vary, it is preferably about 10 cm. The resistivity between L1 and L2 is denoted as R. Also shown in FIG. 1A is a cross-section of the body segment with the interstitial compartment denoted as T and blood vessels denoted as B. Optionally, a means to compress the body segment is provided, for example a pressure cuff 3 that surrounds the body segment. When the body segment is not compressed, for example when the pressure cuff 3 is uninflated, the blood vessels are uncompressed and the resistivity R reflects the resistivity of both the interstitial compartment T and the intravascular compartment B. As shown in FIG. 1B, when the body segment is compressed, for example by inflating the pressure cuff, to a pressure above about the systolic blood pressure, optionally up to about 240 mmHg, the blood vessels are compressed and substantially all of the blood volume contained within the intravascular compartment of the body segment is forced out of the body segment. When the resistivity between the electrodes placed at L1 and L2 is measured under such circumstances, the resistivity value $\rho_1$ represents the resistivity of the interstitial compartment of the body segment.

The principle of measurement of segmental bioimpedance provides a means to measure segmental resistivity and may be explained with reference to FIGS. 1A and 1B. Segmental resistivity is calculated using the formula:

$$\rho_{measure} = AR/L \ (m \cdot \Omega) \qquad \text{Equation 1}$$

Where $\rho_{measure}$ is the measured segmental resistivity; A is the cross-sectional area of the segment ($A = C^2/4\pi$, where C is the circumference of the segment). When no pressure is applied to the body segment the cross sectional area $A_0$ represents the cross sectional area of the body segment including that of the blood vessels, when pressure of at least systolic blood pressure is applied the cross sectional area $A_p$ is that of the body segment minus the cross sectional area of the blood vessels; R is resistance as measured by bioimpedance analysis; and L is the distance between the measurement points (i.e., the distance between measurement electrodes).

The measured resistivity of the body segment depends on a number of factors including the frequency of the injected current and the body mass index (BMI). Preferably a single frequency, and optionally multiple frequencies (multi-frequencies) are used. Injected frequencies from about 1 kHz to about 1000 kHz, more preferably from about 1 kHz to about 50 kHz, most preferably from about 1 kHz to about 10 kHz are utilized. BMI reflects fat content, and is defined as the body weight in kg divided by the square of the height in meters (weight/height$^2$) and is typically measured in kg/m$^2$. In order to distinguish between intravascular and interstitial fluid, preferably the body segment is compressed, optionally by a pressure cuff, preferably a blood pressure cuff (BP cuff) to produce a pressure (P) sufficient to squeeze blood volume out of the studied segment over a few seconds. Thus, two resistivity values can be measured: $\rho_0$ (uncompressed body segment, P=0 mmHg) and $\rho_p$ (body segment is compressed to a pressure from about systolic blood pressure up to $P_{max}$=240 mmHg).

The measurement system comprises a high speed, low noise, acquisition and multi-frequency bioimpedance measurement unit, such as is known to one of ordinary skill in the art, preferably a Xitron 4200s (Xitron Technologies, San Diego, Calif.). Connected to the bioimpedance measurement unit, the system includes an electrical output means attachable to a body segment, the electrical output means preferably comprising at least two injector electrodes for application to a body segment and for the injection of current into the body segment. The system can apply a single frequency of current, or optionally multiple frequencies of electricity (multi-frequencies) ranging from about 1 kHz to about 1000 kHz, more preferably from about 1 kHz to about 50 kHz, most preferably a single frequency from about 1 kHz to about 10 kHz through the injector electrodes. The system further comprises an electrical input means that is adapted to receive the electrical current transmitted from the output means and through the body segment and to then transmit the current to the bioimpedance analysis measurement unit. The input means comprises at least two measurement electrodes for application to the body segment for the receiving and transmission, to the BIA measurement unit, of current transmitted through the selected segment. The electrodes may be made of Ag/AgCl film, conductive rubber, or other appropriate materials which are readily apparent to one of ordinary skill in the art. The injector and measurement electrodes are connected electrically to the BIA measurement unit. This electrical connection may be accomplished by a number of means readily apparent to a person of ordinary skill in the art, but preferably by electrical cables.

In one embodiment of the present invention, the electrodes are incorporated into a pressure cuff suitable for surrounding and compressing the body segment. A single cable optionally may incorporate both the electrical wires to the injector and measurement electrodes and the air tubing connected to the pressure cuff. Such a cable is used to connect the pressure cuff to the measuring unit and an optional air pump. Alternatively, separate electrical cables and a separate air hose may be employed. Optionally, the pressure cuff incorporates a means for electrically measuring the circumference of the body segment. An example of a preferred pressure cuff configuration 3, which is not intended to be limiting in any way is disclosed in FIG. 3. The pressure cuff 3 is a blood-pressure cuff type device that comprises a substantially rectangular form suitable for wrapping around a body segment, such that the body segment is encircled by the device. The pressure cuff is composed of a fabric or other flexible material that preferably is capable of being easily cleaned and/or decontaminated. Material that is suitable will be readily apparent to one of ordinary skill in the art. The pressure cuff also includes a means for securing the device on the body segment, such as a Velcro® system or other such securing system 26, as will be readily apparent to one of ordinary skill in the art. Contained within the pressure cuff 3 is a flexible air-bladder 25 or similar means of compressing the body segment, and applying substantially circumferential pressure of at least about systolic blood pressure to the body segment. The air-bladder is connected to an air hose through which air can be moved to inflate or deflate the air-bladder. The pressure cuff preferably includes at least two injector electrodes 9 and at least two measurement electrodes 10 incorporated therein. The injector and measurement electrodes are electrically connected, preferably by electrical wires 20 and 21 respectively, to a cable connector 27, or other means of electrically connecting the pressure cuff 3 to a bioimpedance measurement unit. At least one, preferably two conductive bands 24 extend substantially the length of the pressure cuff, such that the length of the bands is at least equal to the smallest normal body segment circumference. The bands are composed of a material of stable resistivity. Suitable material includes Cu—Sc alloy or conductive rubber. Other suitable material will be readily apparent to one of ordinary skill in the art. The pressure cuff also comprises at least one and preferably two conductive plates 28 located at the end of the pressure cuff opposite to the end with the securing means 26. The conductive bands 24 and conductive plates 28 are electrically isolated from one another and each is connected, preferably by wires 22 and 23, respectively, to a means of measuring resistivity and/or resistance. The band(s) 24 and plate(s) 28 are arranged on the pressure cuff, such that when the pressure cuff is wrapped around the body segment, the plate(s) 28 electrically connects with the band(s) 24 at a location or locations along the length of the belt such that the distance, measured along the length of the pressure cuff, from the plate(s) 28 to the point of contact on the band(s) 24 is substantially equal to the circumference of the body segment. The circumference of the body segment then can be determined electrically according to the equation:

$$L_{b1} = R1 \times A1/\rho 1$$

Where $L_{b1}$ is the length of the band between the end of the pressure cuff 3 closest to the end where the plate(s) is (are) located and the location at which the plate 28 contacts the band 24;

where R1 is the resistivity of the band between its end closest to the end at which the plate(s) is (are) located and the location at which the plate 28 contacts the band;

where A1 is the cross-sectional area of the band;

and $\rho 1$ is the resistivity of this material.

In this manner, by determining the resistivity of the length of the band(s) that substantially equals the circumference of the body segment, the circumference of the body segment can be determined electrically. In this embodiment, it is preferred that the pressure cuff be securely applied prior to each measurement in order to more accurately measure body segment circumference.

Figure 2:
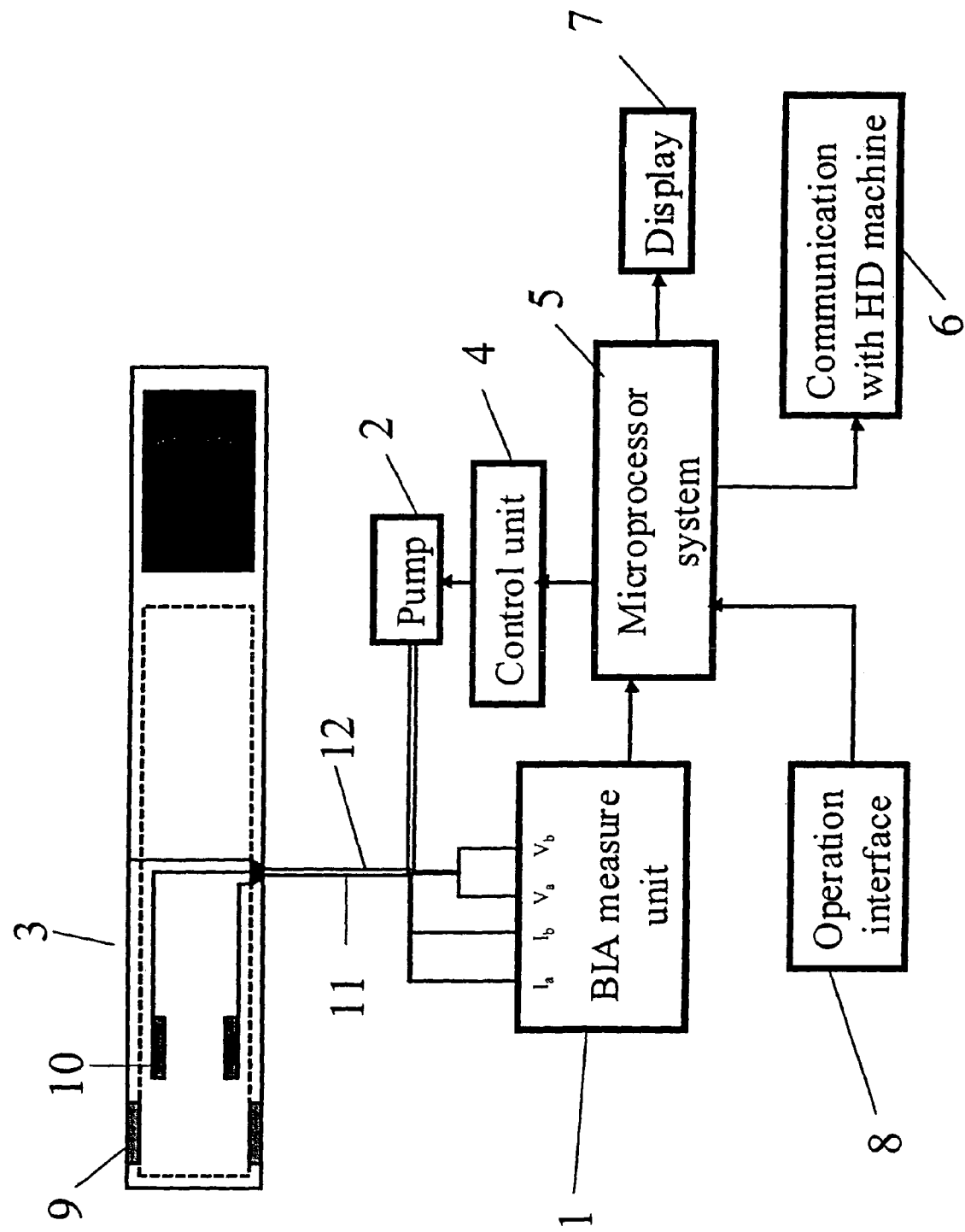
FIG. 2 is a block diagram of a measurement system according to the present invention.

Another embodiment comprises a device for controlling a hemodialysis machine. In this and in other embodiments disclosed herein, an example of a hemodialysis machine suitable for use in or with the invention is that disclosed in U.S. Pat. No. 5,580,460 to Polaschegg. An example, which is not intended to be limiting in any way, is depicted in FIG. 2. In addition to the BIA measurement unit 1, the measurement system also comprises one or more of an air pump 2 to produce pressure to inflate the pressure cuff 3, a control unit 4 to transfer signals from the microprocessor in order to operate the pump, a microprocessor system 5 which is at least a minimal computer with fast data transfer, rapid access and a memory space sufficiently large to permit the manipulation and analysis of the inputted data, a means of communicating with the dialysis machine 6 whereby control signals are sent to and received from the dialysis machine allowing the control of ultrafiltration rate and other hemodialysis parameters according to body hydration status, a display 7 that shows the result of online measurement and an operation interface 8 to input individual patients' parameters to monitor and control dry weight and optionally a means of communication to a standard personal computer (PC) or other device. Optionally, data including, but not limited to, resistance, resistivity, cuff pressure and heart rate is transmitted to the PC by a RS 232 interface or another standard interface in ASCII or other format such that the waveforms of resistivity, pressure values, heart rates and other parameters can be observed, stored, or manipulated on the PC. The block diagram in FIG. 2 shows injector electrodes 9 and measurement electrodes 10, optionally incorporated into the pressure cuff 3. The injector and measurement electrodes are attached, preferably by electrical wiring 11, to the output sockets $I_a$ and $I_b$ and input (measurement) sockets $V_a$ and $V_b$ of the BIA measurement unit 1, and the air pump 2 is connected to the pressure cuff by an air hose 12.

In this embodiment, various patient specific parameters are input into the microprocessor system 5 by means of the operation interface 8. Inputted data and other data optionally are displayed in the display 7. The microprocessor system 5 is connected to the BIA measurement unit 1 by a means of transmitting signals to the BIA measurement unit and signaling the BIA measurement unit to send electrical current to the injector electrodes 9. When such an electrical current is sent through the injector electrodes into the body segment, the current is detected by the measurement electrodes and transmitted back to the BIA measurement unit for processing, the derived data being transmitted to the microprocessor system. The microprocessor system is also connected to the pump control unit 4 which is capable of sending signals to the air pump 2 to inflate and deflate the pressure cuff 3, allowing bioimpedance measurements to be made with the pressure cuff inflated and/or deflated. The microprocessor system is also connected to the hemodialysis machine by a communication means 6, whereby signals can be sent to the hemodialysis machine permitting changes in the hemodialysis procedure, such that the patient's hydration status may be altered.

In one embodiment of the present invention, the ultrafiltration rate is varied by the microprocessor in response to on-line monitoring of the patient's segmental resistivity in order to achieve the patient's proper dry weight or other desired hydration status, and to prevent hypotension during hemodialysis. Optionally, the individual ultrafiltration rate is varied using a time course function related to the slope of changes in segmental resistivity (explained below) during dialysis to optimize the hemodialysis treatment.

The present invention provides a means to determine hemodialysis and peritoneal dialysis patients' dry weight to facilitate the appropriate dialysis prescription. In one preferred embodiment of the present invention segmental bioimpedance is continuously measured in a body segment during hemodialysis. The body segment may be any portion of the body or the entire body, but is preferably a limb segment, more preferably a leg or arm segment, most preferably a calf segment. The relative changes in the value of resistivity is calculated from about every 20 minutes to about every one minute, more preferably about every 10 minutes, even more preferably about every 5 minutes, and most preferably about every minute. The circumference of a body segment, preferably a calf segment or optionally an arm segment, is measured, preferably at the start, optionally at the end of treatment, and preferably intermittently during dialysis, more preferably from about every 10 minutes to about every 20 minutes, in order to derive the cross-sectional area of the segment. Preferably, at least two injector electrodes and at least two measurement electrodes are attached to the body segment. The electrodes may optionally be incorporated within a pressure cuff 3 in the manner set forth above (see, for example, FIG. 3) applied with a pressure cuff and may more preferably be applied as part of a pressure cuff-electrode combination device.

Periodically, current is injected into the body segment through injector electrodes and the current transmitted through the body segment is received by the measurement electrodes. Current from the measurement electrodes then is transmitted to the BIA measurement unit, which determines the resistance of the body segment and optionally transmits the calculated resistance to a microprocessor system that calculates the resistivity according to the method disclosed herein, and which, in turn, may control a hemodialysis machine. Multiple resistivity data points are obtained over time, a curve is derived, and the slope of the curve determined. The slope of the curve approaching zero indicates that a substantially constant resistivity has been achieved, thereby reflecting that dry weight has been substantially attained. As the resistivity curve slope approaches zero, the hydration status of the patient approaches dry weight. Optionally, ultrafiltration may be prolonged or otherwise modified until dry weight is achieved during the ongoing hemodialysis treatment session or hemodialysis may be prolonged during the next hemodialysis treatment to remove the excess fluid and achieve dry weight.

In another embodiment, suitable for both hemodialysis and peritoneal dialysis patients, comparison of the body segment resistivity, preferably post dialysis resistivity, of dialysis patients to the body segment resistivity of healthy subjects is used to determine the patients' hydration status and optionally the appropriate end point for dialysis. The circumference of a body segment is measured, preferably at the start and optionally at the end of treatment. The body segment may be the whole body, a limb segment such as a leg, arm, or other extremity, and is preferably a calf segment. Preferably, at least two injector electrodes 9, at least two measurement electrodes 10, and optionally a pressure cuff 3 are attached to the body segment (see, for example, FIG. 3). Preferably, the electrodes are incorporated within the pressure cuff. At least once, preferably about the time that the dialysis treatment is completed, bioimpedance of the body segment is measured. Optionally, bioimpedance is measured at the start and end of the dialysis treatment, periodically, during most or all of the dialysis treatment, optionally from about every 10 minutes to about every 20 minutes. Bioimpedance is measured optionally with the body segment uncompressed or preferably, with the body segment compressed, preferably by inflation of the pressure cuff. The injection and measurement of current is coordinated to correspond with time points when the pressure cuff is substantially fully inflated or substantially deflated.

To measure resistivity, current is injected into the body segment through injector electrodes and the current transmitted through the body segment is received by the measurement electrodes and transmitted to the BIA measurement unit for calculation of the resistivity of the body segment, the derived data optionally being transmitted to the microprocessor system, according to the method disclosed herein.

To obtain a range of normal resistivity values, the bioimpedance of healthy subjects is measured repeatedly at specific body segments, which may be the whole body, preferably a limb segment, more preferably a leg or an arm segment, most preferably a calf segment, over about 15 minute periods. From these values, a set of normal resistivity values is derived that correlates with dry weights. Preferably a large group of healthy subjects is studied to produce a set of normal resistivity values for a specific population. Optionally, determination of resistivity in subsets of the healthy population can be performed in order to more precisely correlate resistivity values with a dialysis patient's dry weight. For example, because fat mass is often an important factor affecting the measurement of body fluid volumes by bioimpedance analysis, mainly due to the association between the conductivity of skin or fat free mass and the amount of fat, stratification of bioimpedance values according to BMI, gender or age optionally may be undertaken.

At any particular time point, the resistivity of the dialysis patient's body segment is compared to the resistivity of the equivalent body segment in healthy subjects, in order to determine the patient's hydration status. When the resistivity of the dialysis patient's body segment is substantially equal to the resistivity in normal subjects, the dialysis patient is determined to be substantially at dry weight, and preferably the patient's body weight is measured. Subsequently, the patient's body weight measured at a different time point can be compared to the body weight measured at the time that the patient was at about dry weight in order to determine $\Delta W$, the difference between the patient's actual weight and dry weight, and thereby the patient's state of hydration. Using $\Delta W$, the patient's dialysis protocol may be modified so that dry weight is achieved post-dialysis. By way of example, which is not intended to be limiting, if a patient is determined, by comparing resistivity values to those of healthy subjects, to be at dry weight at a mass of X kg, and if at the time of the next dialysis treatment the patient's mass is Y kg and Y>X, then $\Delta W=Y-X$, reflecting the amount of excess fluid to be removed by dialysis to achieve dry weight. Preferably, repeated determinations of dry weight by bioimpedance analysis are performed periodically to provide greater precision in determining the dry weight of a particular patient.

Figure 4:
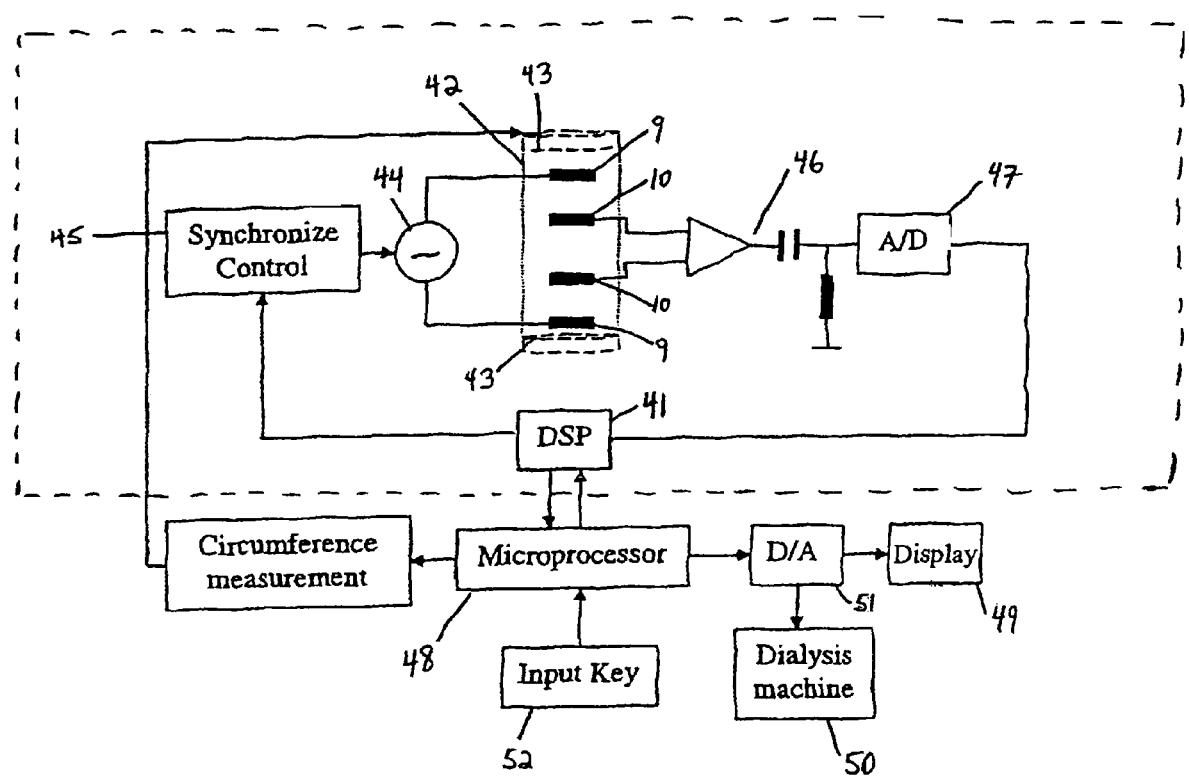
FIG. 4 is a block diagram of a measurement device according to the present invention.

Another embodiment of the present invention comprises a separate device for monitoring the hydration status in a hemodialysis patient, which continuously measures changes in regional resistance and resistivity in a body segment, such as an arm, leg or trunk. Such regional resistance and resistivity measurements are used as a means of assessing change in the extracellular volume using bioimpedance techniques during hemodialysis treatments. A representative example of the device is depicted in FIG. 4. As can be seen in FIG. 4, the device includes: injector electrodes 9 and measurement electrodes 10, each integrated into an electrodes pad 42, which is made from regular adhesive material and contains two conductive wires 43 used to measure segmental circumference; a digital signal processor (DSP) 41 which generates alternate current with different frequencies to be sent to the injector electrodes 9, and pre-processes data from the measurement of voltage from the measurement electrodes 10; a current source 44 which generates different frequencies injected at constant current to the injector electrodes 9; a synchronized control circuit 45 used to synchronize the phase between the current and voltage measured; a measuring circuit 46 which includes amplifier and filter circuits for measuring voltage from the measurement electrodes 10; an A/D converter 47 which converts an analog signal to a digital signal; a microprocessor 48 comprising at least a minimal computer with fast data transfer, rapid access and a memory space sufficiently large to permit the manipulation and analysis of the inputted data, which receives data, calculates, sends results to a display 49, and provides feedback to a dialysis machine 50; a D/A converter 51 which converts a digital signal to an analog signal; a display 49, such as, for example, an LCD display, for displaying the results of online measurement; an input key 52 for inputting individual patients' information for individual treatment; and a dialysis machine 50 which receives and sends control signals allowing for the control of ultrafiltration rates and volumes. In this representative embodiment depicted in FIG. 4, data is transported via the customary means of an electronic patient's cable which connects to injector electrodes 9 and measurement electrodes 10 within the electrode pad 42 on the patient's skin and transports a signal to the DSP 41 and the microprocessor 48 (i.e., through the device), wherein the device itself may be placed within the dialysis machine or may stand alone. When measuring the segmental circumference using the representative embodiment depicted in FIG. 4, the segmental circumference is measured using the same basic principles as were employed when measuring the segmental circumference using the pressure cuff embodiment, as was previously described herein. That is, the segmental circumference (i.e., the circumference of the body segment) is determined electrically according to the equation:

$$L = R \times A/\rho \qquad \text{Equation 2}$$

where L is the length of the conductive wire 43; R is the resistance of the conductive wire 43; A is the cross-sectional area of the conductive wire 43; and $\rho$ is the resistivity of the conductive wire 43.

An alternative representative embodiment of the device for continuously measuring changes in regional resistance and resistivity in a body segment is represented by the dotted line in FIG. 4. That is, this device may also be self-contained within a single unit. The dotted line in FIG. 4 can represent an electrode pad into which the device elements required for measurement (including the measuring circuit 46, the A/D converter 47, and the DSP 41) are fully integrated. Then, digital signals are sent by a cable from this fully integrated electrode pad to another element of the device which is placed in the dialysis machine for further signal processing.

This device according to the present invention is used to monitor the hydration status in a hemodialysis patient, and/or to determine a patient's dry weight. The continuous measuring of changes in regional resistance and resistivity in a body segment, such as an arm, leg or trunk, are used as a means of assessing change in the extracellular volume using bioimpedance techniques during hemodialysis treatments. Specifically, the relative changes in extracellular volume (ECV) in the regional body segment are calculated according to the following equation:

$$\delta = ECV_t/ECV_0 = (\rho \times L^2/R_t)/(\rho \times L^2/R_0) = R^0/R_t \qquad \text{Equation 3}$$

where $ECV_t$ is a variable equal to the resistivity ($\rho$) times the square of the segmental length (L) divided by the resistance ($R_t$) during hemodialysis; $ECV_0$ is a constant value equal to the extracellular volume at the beginning of dialysis. As shown by Equation 3 above, relative changes in the percentage of ECV can be represented by the changes in the ratio of the resistance $R_0$ at the beginning of hemodialysis to the resistance $R_t$ during hemodialysis.

The regional resistivity $\rho$ is calculated according to the following equation:

$$\rho = R \times A/L \, (\Omega\text{cm}) \qquad \text{Equation 4}$$

where R is the extracellular resistance between two measurement electrodes 10; A is the cross sectional area of the regional segment in the body ($A = C^2/4\pi$, where C is the circumference of the segment); and L is the length of the segment between two measurement electrodes 10.

The limitation of the refilling rate threshold is defined as the minimum change in the slope of the curve of $\delta$ according to the following equation:

$$\Delta\delta = (R_0/R_t - R_0/R_{t+1}) \times 100\% \qquad \text{Equation 5}$$

where $\Delta\delta$ is the relative change in the extracellular volume (ECV) during dialysis; R is the resistance during dialysis at time 0 (i.e., the beginning of dialysis); $R_t$ is the resistance during dialysis at time t; and $R_{t+1}$ is the resistance during dialysis at time t+1. Based on the experimental data as described in Example 3, an individual patient should reach his dry weight when $\Delta\delta \leq$ about 2%.

However, an additional step needs to be taken to confirm that the patient has indeed reached his dry weight. Besides a patient reaching his dry weight, there are other reasons for and causes of a change in $\delta$ during dialysis treatment, such as a change in the diameter of vessels in the particular body segment or a variation in cardiac output. Therefore, the measurement of resistivity is necessary to confirm that the patient's dry weight has been reached by comparison with the normal range of resistivity. If and when a patient reaches his dry weight, the resistivity should be represented by the following equation:

$$\text{Resistivity}(\rho) \geq \rho N \qquad \text{Equation 6}$$

where $\rho N$ is the normal range of resistivity ($\rho N = 591 \pm 89$ ($\Omega$cm)) according to previous work (see Zhu et al., *Determination of dry weight in hemodialysis patients by monitoring changes in the slope of extracellular volume (ECV) during dialysis*, ASAIO 48:180 (2002)).

Thus, one embodiment for determining the dry weight of a hemodialysis patient according to the present invention is as follows: calculate $\Delta\delta$ until $\Delta\delta$ is $\leq$ about 2%; then compare $\rho$ to $\rho N$, and if $\rho < \rho N$, then the ultrafiltration rate and treatment time need to be adjusted until $\rho \geq \rho N$, and if $\rho \geq \rho N$, then the dry weight of the hemodialysis patient has been reached. The methods and procedures for adjusting the ultrafiltration rate and treatment time are known in the art and would be understood by one of ordinary skill in the art.

Figures 3, 3A:
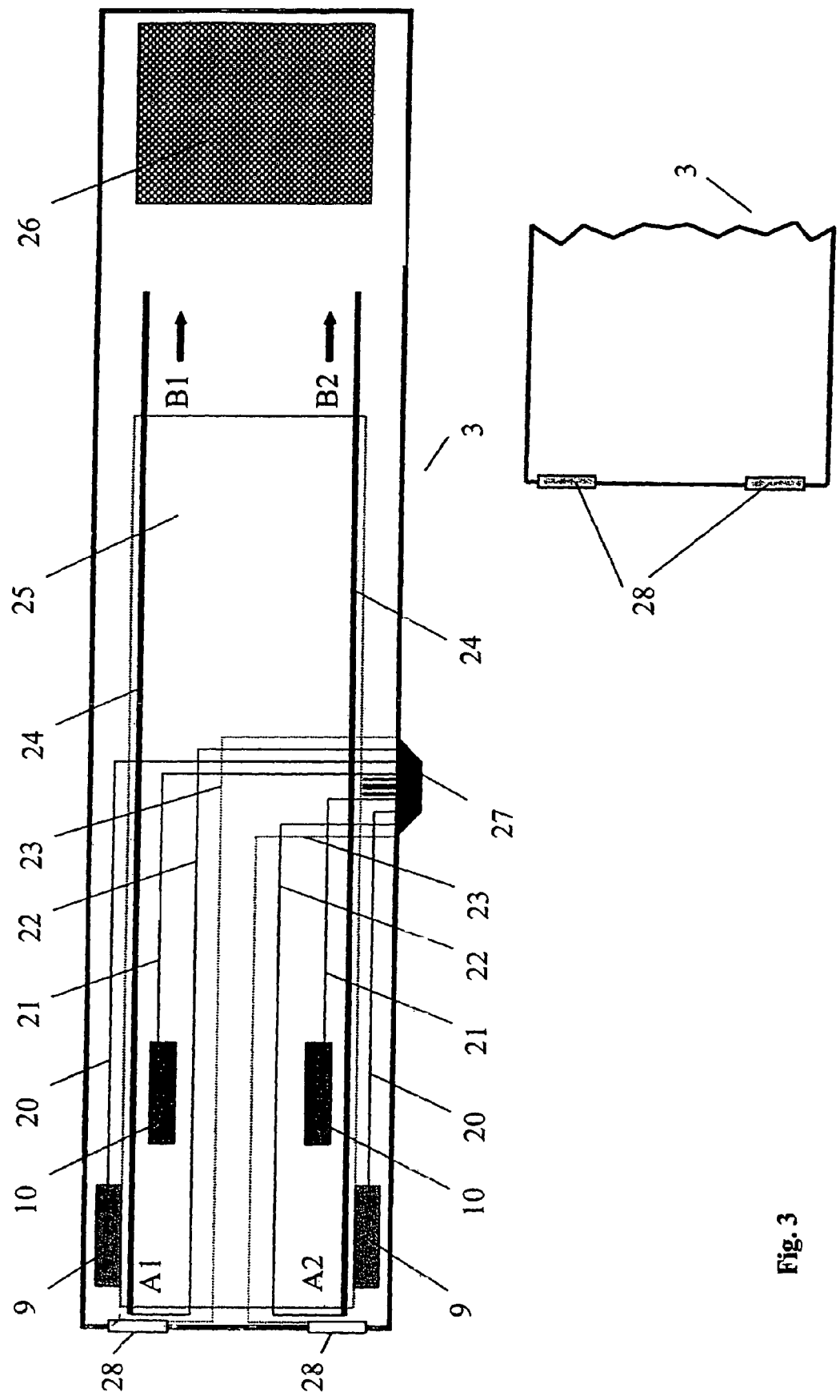
FIG. 3 is a diagram of a pressure cuff for measurement of the circumference of a body segment and for use in measurement of segmental bioimpedance when the body segment is compressed or uncompressed. Shown is a front view with the covering partially cut away, and in FIG. 3A, a partial back view showing the conductive plates.

As described above, representative examples of the device of the invention are depicted in FIGS. 2, 3 and 4. The bioimpedance analysis measurement unit and/or the digital signal processor provides raw data of continuous measurements of resistance, reactance, impedance and/or phase angle with different frequencies. In short, the bioimpedance analysis measurement unit and/or the digital signal processor continuously monitors and measures the bioimpedance parameters of the patient. The extracellular resistance (R) and the intracellular resistance ($R_I$) can be calculated by the Cole-Cole model, which is a well-known model readily understood by one of ordinary skill in the art. The extracellular resistance R of a body segment (such as a calf) corresponds to the extracellular fluid volume (ECV) of the body segment such that a curve of the continuous measurement of the extracellular resistance R can be used to monitor the change in the ECV during dialysis, such as hemodialysis (HD). However, this curve could be affected by a number of factors during dialysis such that it is possible that the noise of the resistance R might be larger than its true signal. To reduce these interferences and the resulting noise, an embodiment of the invention provides for a program of continuously dynamic filtering of such a curve.

As used herein, the term "dialysis" is being used in its broad sense to refer to additional processes beyond hemodialysis. Thus, as used herein the term "dialysis" refers not only to hemodialysis, but also to peritoneal dialysis, etc.

The ratio of $R_i/R_{i+1}$ can be calculated using any two successive data points, where subscript i (i=1, 2, 3, . . . N) represents the ith value of measurement from a series of data which has a total number of N data points. As we want to know the relative change in the extracellular resistance R during dialysis treatment, the R at the start of dialysis is considered as the reference point for the hydration state and it is represented as $R_0$. Thus, the ratio can be written as follows:

$$\lambda(t) = \frac{R_0}{R_t} \qquad \text{Equation 7}$$

where $\lambda$ is a function of time (t), $R_0$ is the extracellular resistance at the start of dialysis, and $R_t$ is the extracellular resistance at time t. Since $R_0$ and $R_t$ corresponds to the ECV at different times, the $\lambda$ function represents the change in ECV during dialysis. It should be noted that with continuous measurement of resistance R, the time t may be at any time during dialysis (e.g., after 20 seconds), and likewise the time period between measurements may be any desired time interval (e.g., a 20-minute time interval $\Delta t$).

The slope ($k_s$) of the function $\lambda(t)$ is defined as the difference between $\lambda(t_1)$ and $\lambda(t_2)$ divided by the time interval $\Delta t$ ($\Delta t=t_2-t_1$), wherein $\Delta t$ is the time interval between any two measurements. The difference between $\lambda(t_1)$ and $\lambda(t_2)$ can be defined as:

$$\delta(\Delta t)=\lambda(t)-\lambda(t+t_m) \qquad \text{Equation 8}$$

wherein $\delta(t)$ represents the difference in value in the function $\lambda(t)$ between two measurements within $t_m$ units of time (such as minutes). Thus, the slope ($k_s$) can be written as follows:

$$k_s = \frac{\delta(\Delta t)}{\Delta t} = [\lambda(t) - \lambda(t+t_m)]/t_m \qquad \text{Equation 9}$$

As we have herein defined, the curve of continuous measurement of the $\lambda(t)$ function is "flattening" as $$\delta(\Delta t) < C_1 \qquad \text{Equation 10}$$

and/or $k_s = \delta(\Delta t)/\Delta t < C_2$ \qquad Equation 11 where $\Delta t = t_m$, representing the time interval between two measurements in units of time (such as minutes), which can be presented in more general form as follows:

$$\Delta t = t_i - t_{i+m}, \qquad \text{Equation 12}$$

where i represents the number of the measurement with i=0, 1, 2, . . . N–m; N represents the total number of measurements; m represents the number of measurements in the time interval $\Delta t$; and $t_m$ represents the time at m measurements. $C_1$ and $C_2$ are constants reflecting the desired and/or required amount of flattening of the $\lambda(t)$ function. Preferably, the $\lambda(t)$ function is deemed to be flattening when the slope ($k_s$) of the $\lambda(t)$ function is less than 0.0005 min$^{-1}$ (i.e., approaching a flat, horizontal line). Thus, with a value of 0.0005 min$^{-1}$ for $C_2$, corresponding values for $C_1$ can be determined for varying values of the time interval $\Delta t$ based on Equations 10 and 11 above. That is, the flattening of the curve is defined by Equations 10 and 11 above. For example, with a value of 0.0005 min$^{-1}$ for $C_2$, and if we let $\Delta t=20$ minutes (a preferred value for $\Delta t$), then the value of $C_1$ should be 0.01 (i.e., (0.0005 min$^{-1}$)·(20 min)). Thus, at any specific time ($t_{i+m}$), when the value of $\delta(\Delta t) < 0.01$ or $\delta(\Delta t)/\Delta t < 0.0005$, the curve during this 20 minutes is considered as flattened.

However, there are many factors which could interfere with the $\delta(\Delta t)$ curve during the measurements. Despite the fact that $\delta(\Delta t) < C_1$ from the start point (i) to the end point (i+m), the determination of flattening might not be correct if the calculation is performed with only two points. To improve the accuracy of the determination of flattening, an algorithm of least squares has been used to confirm the flattening during the time interval.

$$S^2 = \sum_{i}^{N} (y_i - \hat{y}_i)^2 \qquad \text{Equation 13}$$

where $y_i$ is an ideal value which is calculated by linear equation at the ith point; $\hat{y}_i$ is the value of the data by measurement at the same point; N is the total number of measurements in the given period of time ($\Delta t$), for example 20 minutes, during this calculation. The ideal value $y_i$ is calculated by a simple linear equation as follows:

$$y_i = kx_i + y_{i-1} \qquad \text{Equation 14}$$

where k is the slope of the $R_0/R_t$ curve (i.e., $\lambda(t)$) which is defined as follows:

$$k = \frac{y_m - y_i}{x_m - x_i} \qquad \text{Equation 15}$$

where subscript m is the number of measurements during the time interval $\Delta t$ (for example, at 20 minutes after the point of i, in other words, the interval between i and m is 20 minutes: $t_m - t_i = 20$ min). According to the criteria of dry weight, if the curve of $R_0/R_t$ (i.e., $\lambda(t)$) flattens, then the calculated slope should be equal to, for example, 0.01/20 min=0.0005/min. In Equation 15, $x_i$ and $x_m$ are the number of measurements at the time $t_i$ and $t_m$, respectively. To use Equation 14 in practice, since $x_i$ is a constant number and, as an example equal to 1, Equation 14 can be simplified as follows:

$$y_i = y_{i-1} + k \qquad \text{Equation 16}$$

From Equation 15 the value of k should be <0, therefore, the value of $y_i$ is calculated by the difference between the value of k and the previous value of y (i.e., $y_{i-1}$). Finally, the flattening of the curve of the $\lambda(t)$ function can be determined by Equation 17 as follows:

$$\frac{S}{\sqrt{N}} < C_3 \qquad \text{Equation 17}$$

where N is the total number of the measurements (m–i) during the time interval $\Delta t$ (for example, 20 minutes), and $C_3$ is a constant value which depends on the given requirement for precision and is calculated by a least squares error estimation. Preferably, $C_3$ is calculated such that the error in the $\lambda(t)$ function (i.e., the difference between the actual data and the estimated data) is not more than about 1% of the actual value. For example, in one current study if $t_m=20$ min, then $C_3=0.0025$. This algorithm according to Equation 17 can be put into a program to confirm flattening of the curve of the $\lambda(t)$ function.

Furthermore, in accordance with an embodiment of the present invention, a method and device for the continuous measurement of resistance and resistivity to determine a dialysis patient's dry weight is provided, wherein the continuous calculation of the circumference of a body segment is employed. Representative examples of the device are depicted in FIGS. 2, 3 and 4. It should be noted that the device of the invention could be made in a wide variety of sizes and forms. For example, the device could be made to be as small as possible such that it could be used to measure a very small regional area, and it could be a portable, battery-operated device.

As previously described in connection with previous embodiments of the invention, measurement of the electrical resistivity of a body segment can be used to identify a patient's hydration state and is particularly useful for estimation of a dialysis patient's dry weight. As stated above, electrical resistivity ($\rho$) is equal to the resistance (R) measured by the bioimpedance analysis measurement unit times cross-sectional area (A) divided by the length (L) of the body segment of measurement.

$$\rho = \frac{RA}{L} = \frac{R\chi^2}{4\pi L} \qquad \text{Equation 18}$$

The cross-sectional area (A) can be calculated by circumference ($\chi$) squared divided by 4 times pi ($A=\chi^2/(4*\pi)$), where $\chi$ and L can be measured by a tape measure (i.e., by physical means). As this measurement must be performed at the patient's body segment (such as the calf) during dialysis, there is a practical issue which is how to measure the circumference of the body segment when the diameter of the body segment is continuously decreasing. As described above, the length (L) of the body segment (such as the calf) which is the distance between two measuring electrodes is constant, and the circumference ($\chi$) is measured at the start and the end of dialysis. Therefore, in order to obtain the value of resistivity by continuous measurement, a method providing for the continuous and accurate measurement of the circumference of the body segment is needed. In accordance with this embodiment of the invention, a method for obtaining the continuous and accurate measurement of the circumference of the body segment is provided, based upon the continuous measurement of the resistance of the body segment (as described below).

Figure 11:
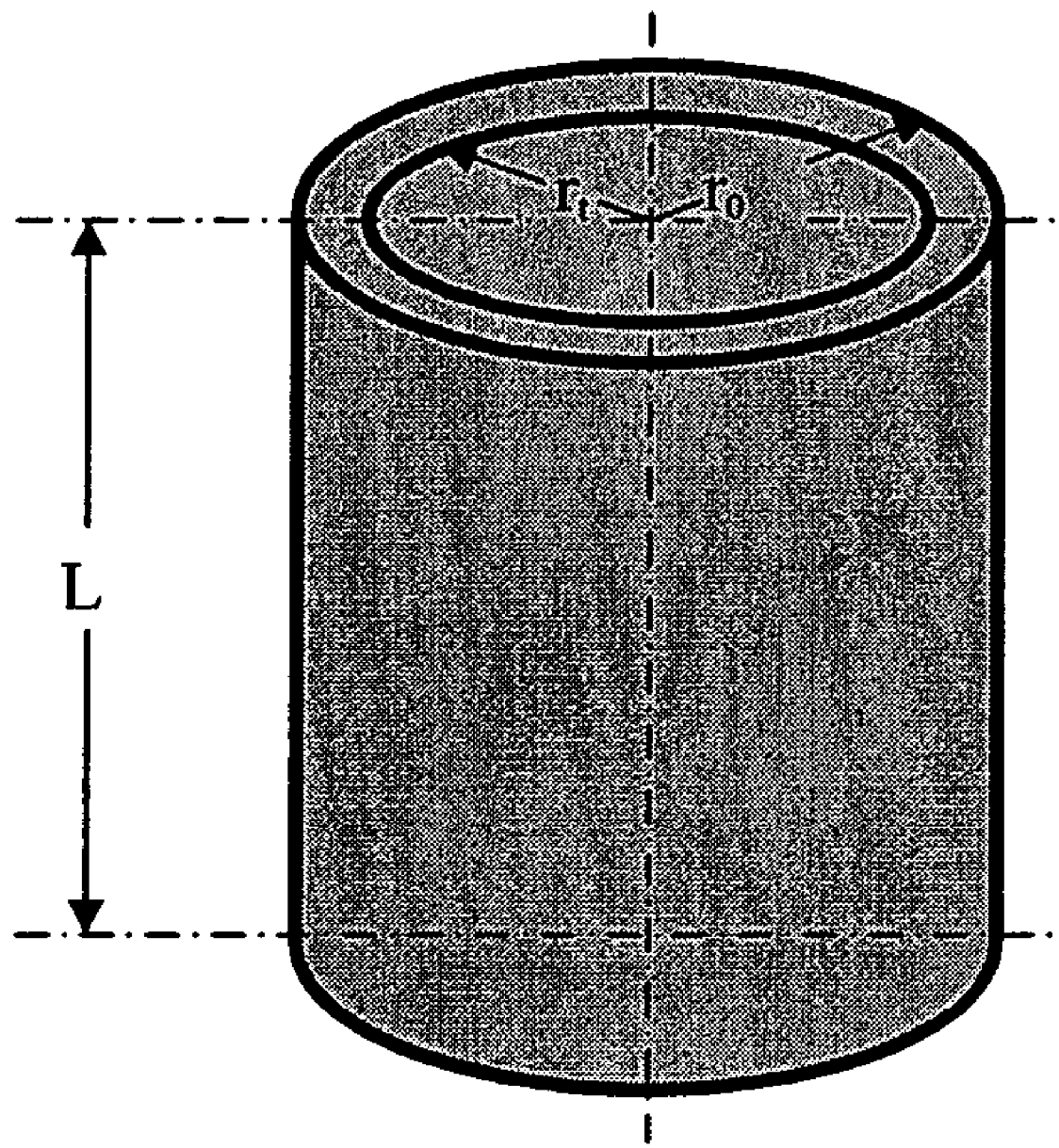
FIG. 11 is a three-dimensional view of a geometrical model of a body segment, such as a calf.

As shown in FIG. 11, a cylinder represents the volume of the body segment, such as the calf, which is measured using the bioimpedance analysis measurement unit and/or the digital signal processor. The calculation is based on an assumption that a change in circumference during dialysis is due to a change in the fluid volume of the body segment, such as the calf. FIG. 11 is a geometrical model of a body segment, such as a calf, wherein $r_0$ is the radius of the segment pre-dialysis, $r_t$ is the radius of the segment during dialysis or at the end of dialysis at a time t, $\chi_0$ is the segment circumference pre-dialysis, $\chi_t$ is the segment circumference during dialysis or at the end of dialysis at a time t, L is the length of the segment, and $\Delta V$ is the change in fluid volume of the segment.

From a geometric point of view, the change in the fluid volume can be written as follows:

$$\Delta V = (\pi r_0^2 - \pi r_t^2)L = \pi L(r_0^2 - r_t^2) = \frac{L}{4\pi}(\chi_0^2 - \chi_t^2) \qquad \text{Equation 19}$$

letting $\Delta r = r_0 - r_t$, $$\Delta V = \pi L(2r_0\Delta r - \Delta r^2) \qquad \text{Equation 20}$$

Since circumference $\chi_0 = 2\pi r_0$ and $\chi_t = 2\pi r_t$, the change in $\chi$ can be calculated by:

$$\Delta\chi = \chi_0 - \chi_t = 2\pi(r_0 - r_t) = 2\pi\Delta r \qquad \text{Equation 21}$$

So, $\Delta r = (\Delta\chi/2\pi)$ and thus change in volume can be calculated by:

$$\Delta V = \frac{2\chi_0\Delta\chi - \Delta\chi^2}{4\pi}L \qquad \text{Equation 22}$$

Equation 22 can be simplified as Equation 23:

$$\chi_0 - \Delta\chi = \sqrt{\chi_0^2 - \frac{4\pi}{L}\Delta V} \qquad \text{Equation 23}$$

In addition, changes in volume also can be calculated by changes in resistance using basic bioimpedance analysis as follows:

$$\Delta V = \rho L^2\left(\frac{1}{R_0} - \frac{1}{R_t}\right) = \rho L^2\left(\frac{R_t - R_0}{R_0 R_t}\right) = \frac{\rho L^2}{R_0}\left(1 - \frac{R_0}{R_t}\right) \qquad \text{Equation 24}$$

where $\rho$ is resistivity, L is the length of the body segment, and $R_0$ and $R_t$ are the extracellular resistances measured by the bioimpedance analysis measurement unit at the start of dialysis and by continuous measurement at a time t during, or at the end of, dialysis, respectively. Finally, the value of circumference at time t ($\chi_t$) can be calculated by combining equations 19 and 24 as follows:

$$\chi_t = \chi_0 - \Delta\chi = \sqrt{\chi_0^2 - \frac{4\pi\rho_0 L}{R_0}\left(1 - \frac{R_0}{R_t}\right)} \qquad \text{Equation 25}$$

where $\chi_0$ and $R_0$ are measured at the start of dialysis, L is set as a constant (e.g., 10 cm), and $\rho_0$ is a constant value of resistivity (e.g., 135 $\Omega\cdot$cm). The constant value for $\rho_0$ can be experimentally determined based on known values of circumference $\chi_0$ and $\chi_t$ (obtained by measuring with a tape measure) and corresponding known, measured values for $R_0$ and $R_t$, such that the constant value for $\rho_0$ can be obtained by a regression analysis. In accordance with Equation 25, the circumference of a body segment can be continuously calculated based on the single variable $R_t$.

Figure 6:
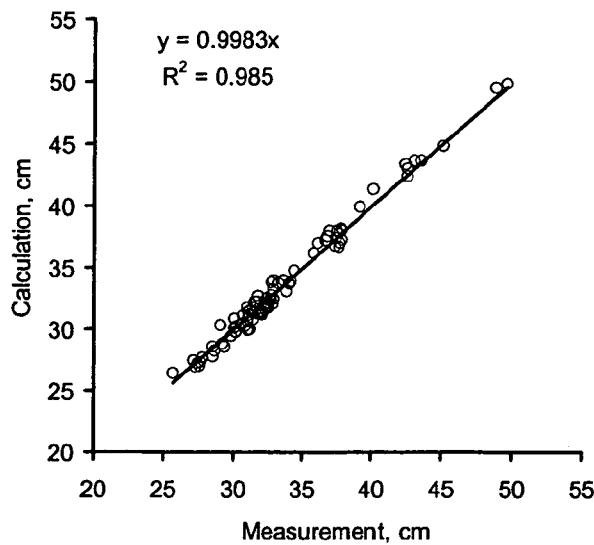
FIG. 6 is a graph of the correlation between physical measurements of the circumference of a body segment and calculations of such circumferences in accordance with an embodiment of the present invention.
Figure 7:
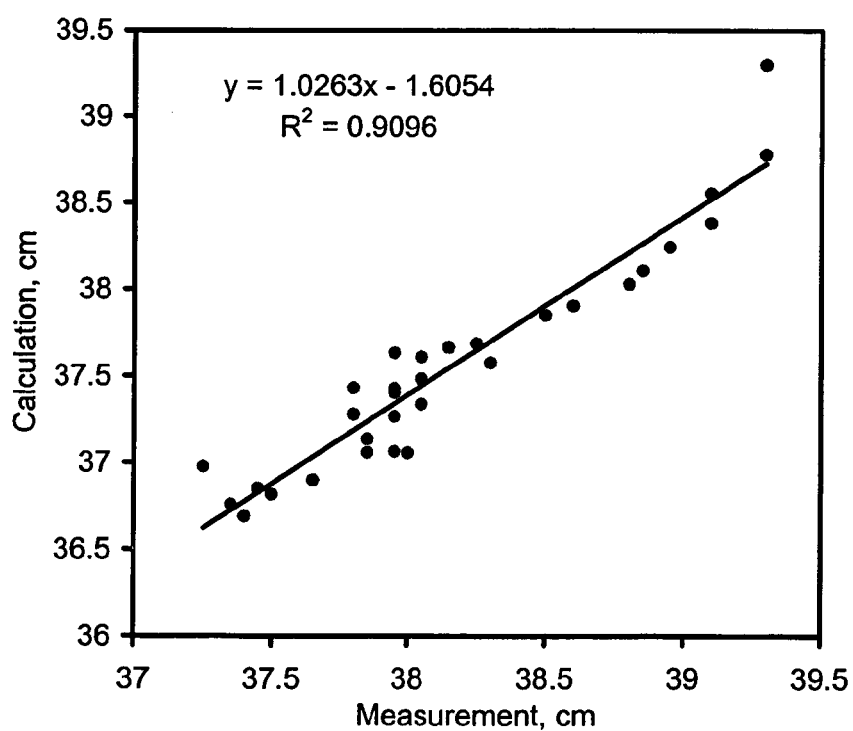
FIG. 7 is a graph of the correlation between physical measurements of the circumference of a body segment and calculations of such circumferences in accordance with an embodiment of the present invention.

Examples of determining the value of circumference at time t ($\chi_t$) can be seen in FIGS. 6 and 7. FIG. 6 shows the correlation between measurements of the circumference of a calf in patients post-dialysis by a tape measure with an accuracy of 0.1 cm, and calculations of such circumferences using Equation 25 (with n (sample size)=90). FIG. 7 shows the correlation between periodic measurements of the circumference of a calf by a tape measure with an accuracy of 0.1 cm every approximately 10 minutes from one patient during a hemodialysis treatment, and calculations of such circumferences using Equation 25.

Therefore, the value of resistivity at the body segment, such as a calf, as a function of time can be calculated according to Equations 18 and 25 above, as follows:

$$\rho(t) = \frac{\chi_t^2 \cdot R_{5,t}}{4\pi L} \Omega \cdot cm \qquad \text{Equation 26}$$

where $\rho(t)$ is the resistivity by continuous measurement (i.e., resistivity as a function of time), $\chi_t$ represents the circumference of the body segment at time t according to Equation 25, and $R_5$ is the resistance measured at 5 kHz frequency (wherein 5 kHz is an exemplary frequency only, and other frequencies may be employed as described above).

The continuous measurement of the resistivity $\rho(t)$ at the body segment could be utilized in several different applications. As a change in resistivity is associated with a change in the regional body fluid volume in the segment, the continuous measurement of the resistivity $\rho(t)$ could be used to monitor the degree of bleeding within a segment as regional bleeding would make the regional body fluid volume increase such that the resistivity $\rho(t)$ would decrease. In addition, this continuous measurement of the resistivity $\rho(t)$ provides for a method to measure the change in conductivity of a body segment, which for example, could be used to indicate the blockage of a blood vessel due to differing conductivities between blood and a blocking thrombus. Thus, this continuous measurement of the resistivity $\rho(t)$ may be particularly useful in monitoring the access flow, and in detecting clotting of the access, for a dialysis patient.

In order to compare the resistivity and reduce the variation, normalized resistivity is defined as:

$$\rho_N(t) = \frac{\rho(t)}{BMI} \times 10^{-2} \Omega \cdot m^3/kg \qquad \text{Equation 27}$$

where BMI is the body mass index defined as body weight (wt) divided by body height (h) squared. Since we know the range of normalized resistivity in healthy subjects, the patient's normal hydration level can be obtained by comparing the minimal level of normalized resistivity, which is given by Equation 28:

$$\rho_N(t) \geq \rho_{N,H} \qquad \text{Equation 28}$$

where $\rho_N(t)$ represents the patient's value of normalized resistivity as a function of time and $\rho_{N,H}$ represents a minimal level of normalized resistivity in healthy subjects. Exemplary values for $\rho_{N,H}$ are $18.3 \times 10^{-2}$ $\Omega \cdot m^3/kg$ for males and $20 \times 10^{-2}$ $\Omega \cdot m^3/kg$ for females.

Figure 8:
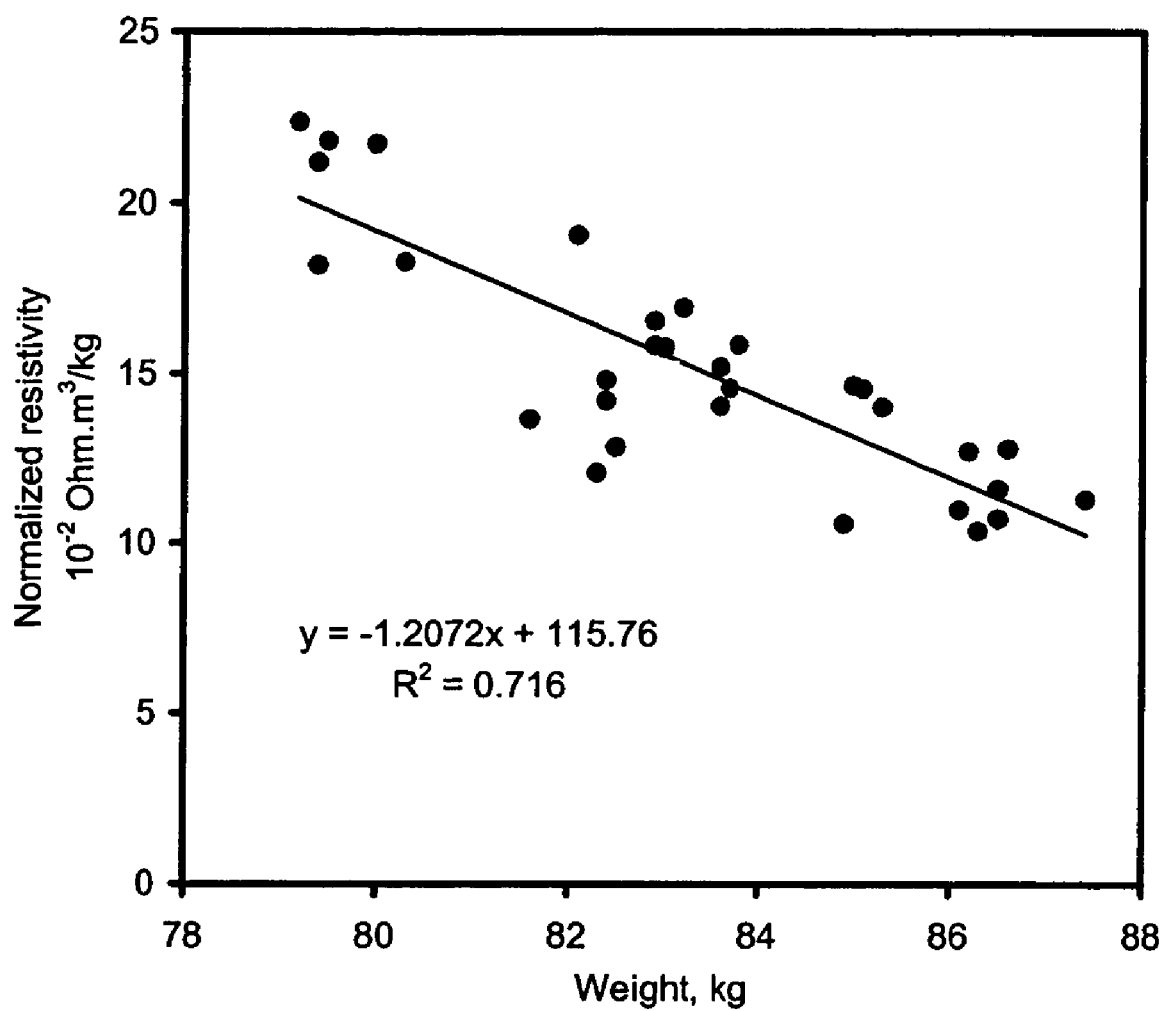
FIG. 8 is a graph of the correlation between a patient's body weight and a patient's value of normalized resistivity $\rho_N(t)$ for a body segment in accordance with an embodiment of the present invention.

As can be seen in the example depicted in FIG. 8, a patient's value of normalized resistivity $\rho_N(t)$ for a body segment (a calf in FIG. 8) reflects the patient's body weight as shown such that the hydration state of the patient's total body may be monitored by tracking the variable $\rho_N(t)$.

In addition, body weight ($W_t$) can be continuously calculated according to the following equation:

$$W_t = W_{pre} - \sum_i UFR_i \times \Delta t_i \qquad \text{Equation 29}$$

where $W_{pre}$ represents pre-dialysis body weight, UFR represents the ultrafiltration rate, $\Delta t$ is the period of time with a constant UFR and subscript i represent ith period of time with a constant UFR. The dry weight (DW) of a patient can also be calculated in a general and continuous form as follows:

$$DW = W_{pre} - \int_{t_0}^{t_{DW}} UFR(t) \cdot dt \qquad \text{Equation 30}$$

where UFR(t) represents the ultrafiltration rate (UFR) as a function of time during dialysis with $t_0$ to $t_{DW}$ being the time interval of a functioning UFR in which $t_0$ is the start time of dialysis and $t_{DW}$ is the time at which the dry weight of the patient is achieved. In order to obtain a numerical result, we assume that the initial start time of dialysis $t_0$ is zero. Once the patient is at the dry weight, in subsequent treatments, the ultrafiltration volume will be obtained by the pre-dialysis body weight ($W_{pre}$) minus the dry weight (DW).

According to Equation 29 and Equation 30 above, the accurate estimation of dry weight depends on how accurately one determines the time at which the dry weight of the patient is achieved ($t_{DW}$). Principally, the $t_{DW}$ is determined by two criteria: 1) $\delta(\Delta t) < C_1$ (Equation 10) or $k_s = \delta(\Delta t)/\Delta t < C_2$ (Equation 11) within $t_m$ units of time (such as minutes) during dialysis; and 2) $\rho_{N,P}$ is equal to or larger than $\rho_{N,H}$ (Equation 28). An algorithm which can be used to identify the dry weight (DW) of the patient and the time at which the dry weight of the patient is achieved ($t_{DW}$) is shown in FIG. 5.

Figure 5:
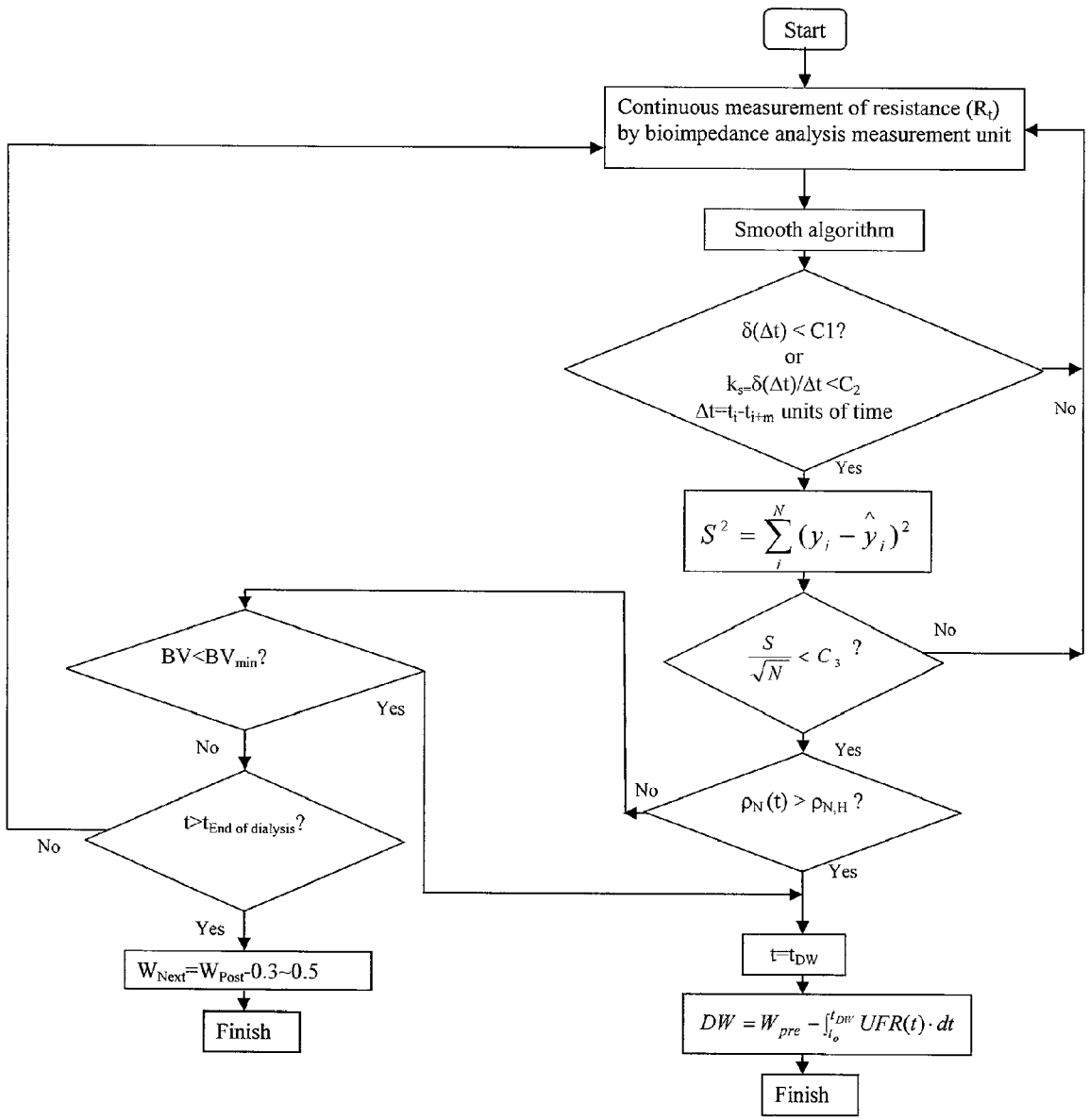
FIG. 5 is an algorithm describing a method to determine the time at which a patient has reached the dry weight ($t_{DW}$), and to determine the patient's dry weight (DW).

As can be seen in FIG. 5, the extracellular resistance $R_t$ is continuously measured by the bioimpedance analysis measurement unit and/or the digital signal processor, and the flattening (i.e., filtering) of the $\lambda(t)$ function is performed in accordance with Equations 10, 11, 13 and 17 as described above. Once the $\lambda(t)$ function is successfully flattened (i.e., filtered), then the patient's value of normalized resistivity as a function of time ($\rho_N(t)$) is compared to a minimal level of normalized resistivity in healthy subjects ($\rho_{N,H}$) according to Equation 28 above. If $\rho_N(t) \geq \rho_{N,H}$, then the dry weight has been achieved (i.e., $t = t_{DW}$), and the dry weight DW can be calculated in accordance with Equation 30 above. If $\rho_N(t)$ is not equal to or greater than $\rho_{N,H}$, then blood volume (BV) of the patient is compared to a minimum blood volume ($BV_{min}$) of the patient, and if $BV \geq BV_{min}$ and the end of the dialysis treatment has not yet been reached, then the algorithm begins again with the continuous measurement of the extracellular resistance $R_t$ by the bioimpedance analysis measurement unit. An exemplary value of $BV_{min}$ is about 70-75% of the patient's normal blood volume; however, $BV_{min}$ may vary from patient to patient, as would be understood by one of ordinary skill in the art. However, if $BV \geq BV_{min}$ and the end of the dialysis treatment has been reached, then a predictive dry weight ($W_{next}$), for the next dialysis treatment, is calculated by subtracting approximately 0.3 to 0.5 kg from the post-dialysis body weight. On the other hand, if $BV < BV_{min}$, then hypotension is occurring (with a less than minimum blood volume), and the dry weight (DW) has been reached and can be calculated in accordance with Equation 30 above. In such a case, the ultrafiltration rate (UFR) must be controlled to a relatively lower value, for example, less than about 800 ml/h.

Figure 9:
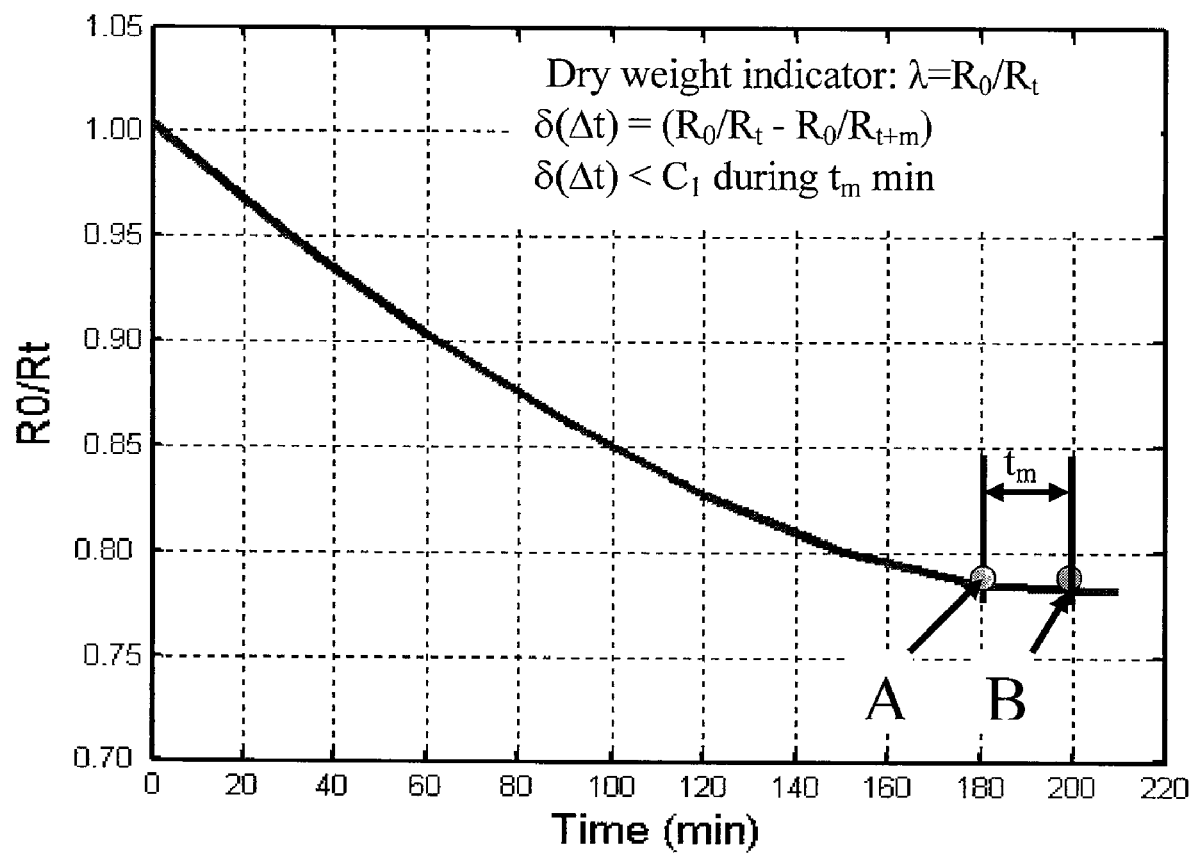
FIG. 9 is a graph of $R_0$ (the extracellular resistance at the start of dialysis)/$R_t$ (the extracellular resistance at time t) as a function of time (i.e., $\lambda(t)$) in accordance with an embodiment of the present invention.
Figure 10:
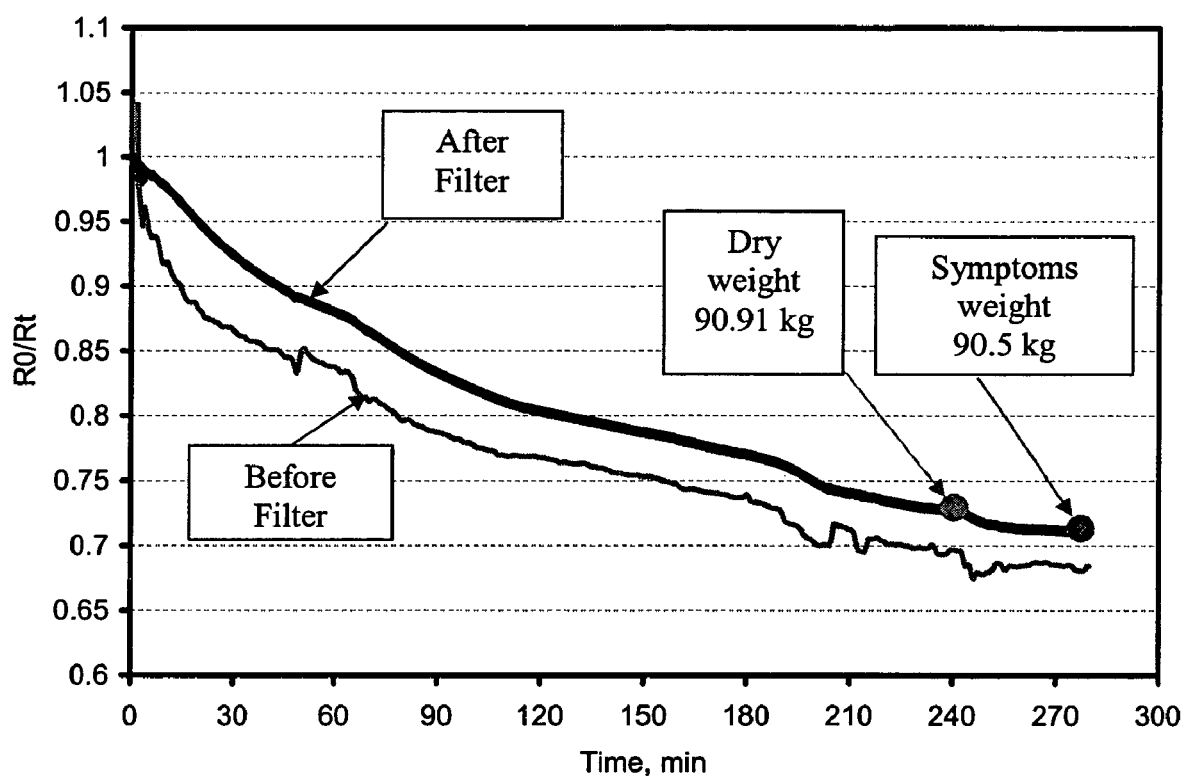
FIG. 10 is a graph of $R_0$ (the extracellular resistance at the start of dialysis)/$R_t$ (the extracellular resistance at time t) as a function of time (i.e., $\lambda(t)$) in accordance with an embodiment of the present invention.

FIGS. 9 and 10 show exemplary embodiments of the present invention wherein the dry weight is determined from a graph of $R_0/R_t$ as a function of time (i.e., $\lambda(t)$). In FIG. 9, the dry weight of a patient is indicated by point B (200 minutes), wherein $\lambda(180 \text{ min})-\lambda(200 \text{ min})<0.01$ over the time interval $t_m=20$ min, and $\rho_N(t) \geq \rho_{N,H}(20 \times 10^{-2} \, \Omega\text{m}^3/\text{kg})$. In FIG. 10, in accordance with an embodiment of the invention, the dry weight of a patient during hemodialysis is determined to be 90.91 kg. In this example of FIG. 10, in order to confirm the dry weight by clinical symptoms, this patient was continuously dialyzed and ultrafiltrated after his dry weight was identified. At the end of the dialysis, the patient experienced symptoms at a weight of 90.5 kg, thereby demonstrating that the excess fluid had been completely removed. In addition, the graph of FIG. 10 shows that the curve after being filtered or flattened in accordance with Equations 10, 11, 13 and 17 (thick line) is smoother, more reliable, and more accurate than the curve before being filtered or flattened (fine line).

Thus, an embodiment of the method and device of the present invention for determining the dry weight (DW) of a dialysis patient and the time at which the dry weight of the patient is achieved ($t_{DW}$) is depicted in FIG. 5.

EXAMPLES

Listed below are a series of examples of the present invention. The examples contained herein are intended to illustrate, but are not intended to limit the scope of the invention.

Example 1

Twenty healthy subjects (Table 1) and thirteen hemodialysis patients (Table 2) were studied, the latter during hemodialysis. Shown in Tables 1 and 2 are their mean ages, weights and body mass indices (BMI). Data are presented as mean value±SD

TABLE 1

| Healthy subjects | | | | |
|---|---|---|---|---|
| | n | Age (years) | Weight (kg) | BMI (kg/m²) |
| Male | 10 | 40.8 ± 5 | 83.1 ± 21.6 | 27.1 ± 5.0 |
| Female | 10 | 35 ± 9 | 64.3 ± 9.7 | 24.2 ± 3.2 |

TABLE 2

| Hemodialysis patients | | | | |
|---|---|---|---|---|
| | n | Age (year) | Dry Weight (kg) | BMI (kg/m²) |
| Male | 10 | 48.5 ± 12.8 | 76.8 ± 16.4 | 26.8 ± 4.3 |
| Female | 3 | 65 ± 14 | 60.5 ± 16 | 23.7 ± 3.5 |

Example 2

Figure 12:
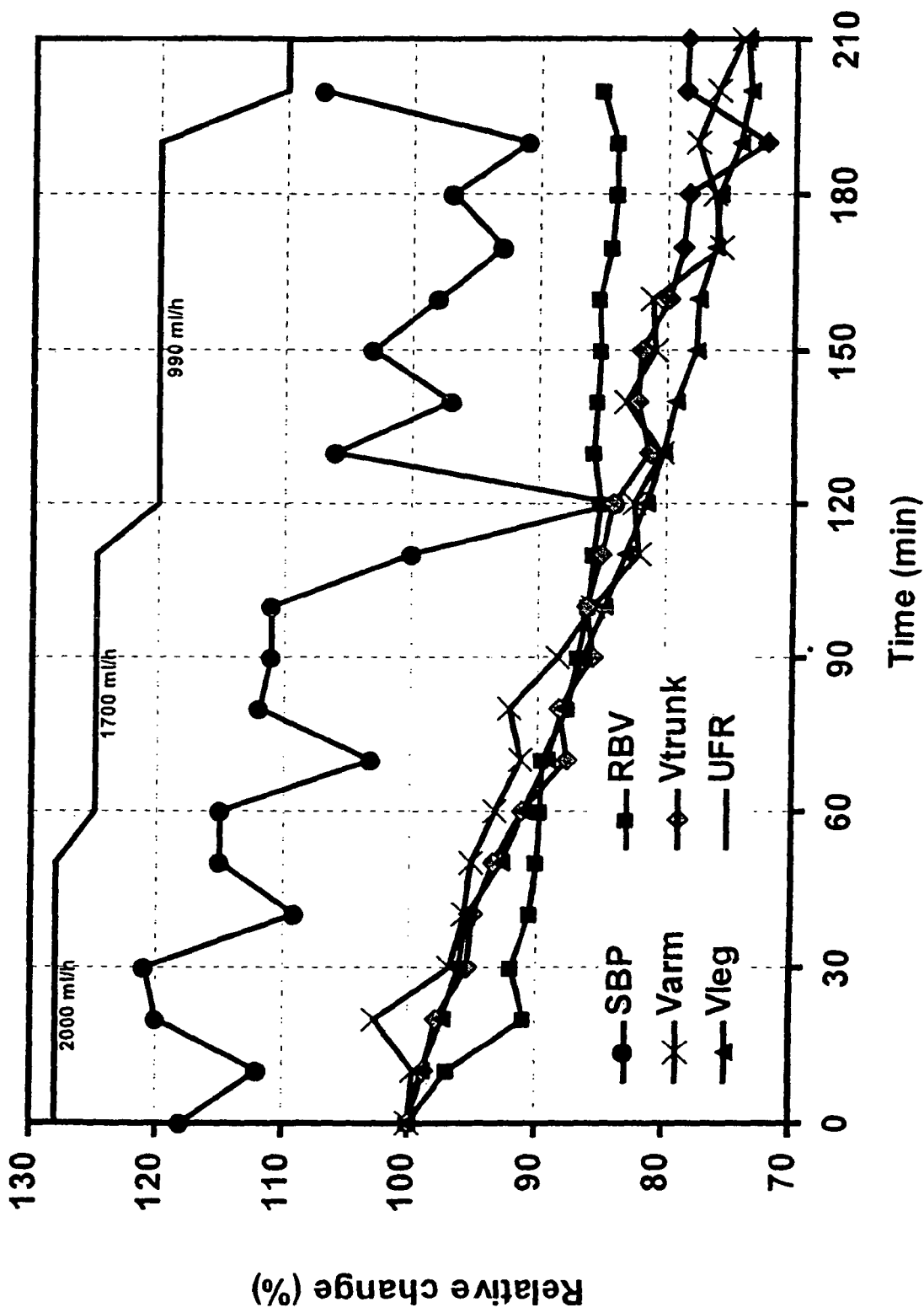
FIG. 12 is a graph of relative changes in systolic blood pressure, ultrafiltration rate, resistivity of different body segments, and relative blood volume over time during hemodialysis.

Segmental bioimpedance was measured continuously every 10 minutes during hemodialysis using 6 electrodes all on the left side of the body. Two electrodes, one on the hand and one on the foot, were used to inject current. Measurement electrodes were placed on the wrist, shoulder, hip and ankle. Resistivity was measured in the wrist-shoulder segment (Varm), the shoulder-hip segment (Vtrunk), and in the ankle-hip segment (Vleg). Also measured were systolic blood pressure (SBP), relative blood volume or hematocrit (RBV), and the ultrafiltration rate (UFR). In this way, blood volume and segmental extracellular volume (ECV) in the leg, arm and trunk were calculated. The results are shown in FIG. 12. The X-axis is time in minutes, the Y-axis the relative change in value with the value of a particular parameter at the start of hemodialysis being equal to 100%. After continuing ultrafiltration changes in ECV of the leg became small that the slope was nearly horizontal i.e. approached 0, which indicates that little fluid was available for ultrafiltration and dry weight had been achieved. Comparing the curves of ECV trunk, leg and arm, it can be seen that the leg is the preferred body segment for dry weight analysis.

Example 3

In this example, we studied 21 hemodialysis patients, dividing them into two groups by clinical estimation of whether they were at clinical dry weight (CDW; number of patients=10, mean age=56.6 years) or were over hydrated (OH; number of patients=11, mean age=66.5 years) (see Table 3 below). For each hemodialysis patient, we measured the resistivity and the rate of change in resistance ($\Delta$ slope, or $\Delta\delta$) during a dialysis session, for a particular body segment. The ratio of regional extracellular volume (ECV) was measured by segmental bioimpedance and compared to regional geometric volume (RGV) for estimation of regional hydration (wherein RGV=cross sectional area (A)·length (L, 10 cm)). Our results, as shown in Table 3 below, indicate that the overhydrated patients (OH) had significantly lower resistivity than the clinical dry weight patients (CDW); however, the rate of change in resistance ($\Delta$ slope) during dialysis was not significantly different between the overhydrated patients (OH) and the clinical dry weight patients (CDW). We then adjusted the dry weight target in the clinical dry weight patients (CDW) and measured the resistivity as well as the rate of change in resistance ($\Delta$ slope) during a subsequent dialysis treatment designed to remove more fluid. The resistivity increased further and $\Delta$ slope decreased by half an order of magnitude, accompanied by a significant decrease in blood pressure, weight and ratio of regional extracellular volume to regional geometric volume (ECV/RGV). Although resistivity increased significantly in the CDW patients following further ultrafiltration, both of these values for resistivity were not significantly different from normal (580±60 ohm·cm). Therefore, it appears that measurement of the rate of change in resistance (a slope) is superior to an absolute measurement of resistivity in determining when dry weight is achieved. This suggests that objective dry weight could be identified for individual patients by measuring the rate of change in resistance during dialysis treatments providing a segmental-bioimpedance dry weight (BIA-DW), a weight corresponding to a more normal state of hydration. That is, the CDW group, which hadn't quite reached dry weight, had a $\Delta$ slope value of 2.3±0.21%, or 2.09% to 2.51%. Therefore, if a patient had reached his dry weight, the $\Delta$ slope value should be less than or equal to about 2%.

TABLE 3

| | | Hemodialysis patients | | | | |
|---|---|---|---|---|---|---|
| | $\rho$ ($\Omega \cdot$ cm) | Post ECV/RGV (L/cm$^3$) | $\Delta$ slope (%) | $\Delta$RBV (%) | Pre-MAP (mm Hg) | Post-Wt (kg) |
| OH | 383.4 ± 134 | 0.25 ± 0.08 | 2.2 ± 0.6 | 109 ± 13 | 86.3 ± 10 | 66.2 ± 11 |
| CDW | 524.6 ± 113 | 0.19 ± 0.03 | 2.3 ± 0.21 | 123 ± 19 | 97 ± 15 | 89.6 ± 28 |
| BIA-DW | 609.8 ± 153 | 0.17 ± 0.03 | 0.73 ± 0.5 | 118 ± 16 | 93.6 ± 12 | 88.3 ± 28 | wherein: RBV is relative blood volume; and MAP is mean arterial pressure.

Throughout this application, various articles and patents are referenced. Disclosures of all of these publications are hereby incorporated herein by reference in their entireties. The present invention may be embodied in other forms without departing from the spirit or essential attributes thereof and accordingly reference should be made to the claims rather than to the foregoing specification as indicating the scope thereof.

We claim:

1. A method for determining a dialysis patient's dry weight comprising the steps of:
   continuously measuring the extracellular resistance of a body segment using a plurality of electrodes, while applying a pressure to the body segment, during dialysis and graphing the ratio of $R_0/R_t$ as a function of time, wherein $R_0$ is the extracellular resistance at the start of dialysis and $R_t$ is the extracellular resistance as a function of time;
   using a microprocessor to perform each of the following steps:
   flattening the graph of the ratio of $R_0/R_t$ as a function of time;
   comparing the patient's normalized resistivity as a function of time ($\rho_N(t)$) to a minimum level of normalized resistivity in healthy subjects ($\rho_{N,H}$);
   identifying the time at which the dry weight of the patient has been achieved when $\rho_N(t) \geq \rho_{N,H}$; and calculating the patient's dry weight.

2. The method of claim 1, wherein the patient's normalized resistivity as a function of time ($\rho_N(t)$) is calculated according to the following equation:

$$\rho_N(t) = \frac{\rho(t)}{BMI} \times 10^{-2} \Omega \cdot m^3/kg$$

wherein BMI is the patient's body mass index defined as body weight divided by body height squared; and $\rho(t)$ is the resistivity of the body segment as a function of time, calculated according to the following equation:

$$\rho(t) = \frac{\chi_t^2 \cdot R_t}{4\pi L} \Omega \cdot cm$$

wherein L is the length of the body segment; and $\chi_t$ is the circumference of the body segment as a function of time which is continuously calculated according to the following equation:

$$\chi_t = \sqrt{\chi_0^2 - \frac{4\pi \rho_0 L}{R_0}\left(1 - \frac{R_0}{R_t}\right)}$$

wherein $\chi_0$ is the initial circumference of the body segment; and $\rho_0$ is a constant value of resistivity.

3. The method of claim 2, wherein the patient's dry weight (DW) is calculated according to the following equation:

$$DW = W_{pre} - \int_{t_0}^{t_{DW}} UFR(t) \cdot dt$$

where $W_{pre}$ is the patient's body weight prior to dialysis; UFR(t) is the ultrafiltration rate (UFR) as a function of time during dialysis, with $t_0$ to $t_{DW}$ being the time interval of a functioning UFR in which $t_0$ is the start time of dialysis and $t_{DW}$ is the time at which the dry weight of the patient is achieved.

4. The method of claim 3, wherein the flattening of the graph of the ratio of $R_0/R_t$ as a function of time is achieved during a time interval $\Delta t$ in accordance with at least one of the following equations:

$\delta(\Delta t) < C_1$;

and $k_s = \delta(\Delta t)/\Delta t < C_2$;

wherein $\lambda(t) = R_0/R_t$; $\delta(\Delta t) = \lambda(t) - \lambda(t+\Delta t)$; and $C_1$ and $C_2$ are constants; and
wherein the flattening of the graph of the ratio of $R_0/R_t$ as a function of time is confirmed during the time interval $\Delta t$ by an algorithm of least squares.

5. A device for determining the dry weight of a dialysis patient comprising:
   a digital signal processor;
   an electrical output means being in electrical communication with the digital signal processor and being attachable to a body segment, the electrical output means being adapted to apply electrical current to the body segment;
   an electrical input means being in electrical communication with the digital signal processor and being attachable to a body segment, the electrical input means being adapted to receive the current transmitted through the body segment and transmit the same to the digital signal processor;
   a compression means being in electrical communication with the digital signal processor, said compression means adapted to apply pressure to the body segment; and a microprocessor being in electrical communication with the digital signal processor;

wherein the microprocessor is configured to determine a dialysis patient's dry weight by:

continuously measuring an extracellular resistance of the body segment during dialysis and graph the ratio of $R_0/R_t$ as a function of time, wherein $R_0$ is the extracellular resistance at the start of dialysis and $R_t$ is the extracellular resistance as a function of time;

flattening the graph of the ratio of $R_0/R_t$ as a function of time;

comparing the patient's normalized resistivity as a function of time ($\rho_N(t)$) to a minimum level of normalized resistivity in healthy subjects ($\rho_{N,H}$); and identifying the time at which the dry weight of the patient has been achieved when $\rho_N(t) \gtrsim \rho_{N,H}$.

6. The device of claim 5, wherein the patient's normalized resistivity as a function of time ($\rho_N(t)$) is calculated according to the following equation:

$$\rho_N(t) = \frac{\rho(t)}{BMI} \times 10^{-2} \Omega \cdot m^3/kg$$

wherein BMI is the patient's body mass index defined as body weight divided by body height squared; and $\rho(t)$ is the resistivity of the body segment as a function of time, calculated according to the following equation:

$$\rho(t) = \frac{\chi_t^2 \cdot R_t}{4\pi L} \Omega \cdot cm$$

wherein L is the length of the body segment; and $\chi_t$ is the circumference of the body segment as a function of time which is continuously calculated according to the following equation:

$$\chi_t = \sqrt{\chi_0^2 - \frac{4\pi \rho_0 L}{R_0}\left(1 - \frac{R_0}{R_t}\right)}$$

wherein $\chi_0$ is the initial circumference of the body segment; and $\rho_0$ is a constant value of resistivity.

7. The device of claim 6, wherein the patient's dry weight (DW) is calculated according to the following equation:

$$DW = W_{pre} - \int_{t_0}^{t_{DW}} UFR(t) \cdot dt$$

where $W_{pre}$ is the patient's body weight prior to dialysis; UFR(t) is the ultrafiltration rate (UFR) as a function of time during dialysis, with $t_0$ to $t_{DW}$ being the time interval of a functioning UFR in which $t_0$ is the start time of dialysis and $t_{DW}$ is the time at which the dry weight of the patient is achieved.

8. The device of claim 7, wherein the flattening of the graph of the ratio of $R_0/R_t$ as a function of time is achieved during a time interval $\Delta t$ in accordance with at least one of the following equations:

$\delta(\Delta t) < C_1$;

and $k_s = \delta(\Delta t)/\Delta t < C_2$;

wherein $\lambda(t) = R_0/R_t$; $\delta(\Delta t) = \lambda(t) - \lambda(t+\Delta t)$; and $C_1$ and $C_2$ are constants; and wherein the flattening of the graph of the ratio of $R_0/R_t$ as a function of time is confirmed during the time interval $\Delta t$ by an algorithm of least squares.

9. The device of claim 5, wherein said compression means is a pressure cuff.

* * * * *

UNITED STATES PATENT AND TRADEMARK OFFICE
CERTIFICATE OF CORRECTION

PATENT NO. : 7,801,598 B2  
APPLICATION NO. : 11/246635  
DATED : September 21, 2010  
INVENTOR(S) : Fansan Zhu et al.

Page 1 of 1

It is certified that error appears in the above-identified patent and that said Letters Patent is hereby corrected as shown below:

In the Specifications:

Column 13, line 58, please change " $\delta = ECV_t/ECV_0 = (\rho \times L^2/R_t)/(\rho \times L^2/R_0) = R^0/R_t$ " to -- $\delta = ECV_t/ECV_0 = (\rho \times L^2/R_t)/(\rho \times L^2/R_0) = R_0/R_t$ --

Signed and Sealed this  
Fourteenth Day of May, 2013

Teresa Stanek Rea  
*Acting Director of the United States Patent and Trademark Office*